(12) United States Patent
Kim et al.

(10) Patent No.: US 8,153,155 B2
(45) Date of Patent: *Apr. 10, 2012

(54) ARGININE-CONJUGATED BIOREDUCIBLE POLY(DISULFIDE AMINE) POLYMERS FOR GENE DELIVERY SYSTEM

(75) Inventors: Sun Hwa Kim, Seoul (KR); Ji Hoon Jeong, Gyeonggi-do (KR); Tae-il Kim, Salt Lake City, UT (US); Sung Wan Kim, Salt Lake City, UT (US); David A. Bull, Salt Lake City, UT (US)

(73) Assignee: University of Utah, Salt Lake City, UT (US)

( * ) Notice: Subject to any disclaimer, the term of this patent is extended or adjusted under 35 U.S.C. 154(b) by 176 days.

This patent is subject to a terminal disclaimer.

(21) Appl. No.: 12/496,568

(22) Filed: Jul. 1, 2009

(65) Prior Publication Data

US 2010/0010067 A1     Jan. 14, 2010

Related U.S. Application Data

(63) Continuation-in-part of application No. 12/370,515, filed on Feb. 12, 2009, now abandoned.

(60) Provisional application No. 61/028,131, filed on Feb. 12, 2008.

(51) Int. Cl.
    *A61K 9/14*          (2006.01)
    *C07H 21/04*      (2006.01)

(52) U.S. Cl. ........................ 424/486; 536/23.1; 536/24.5
(58) Field of Classification Search ........................ None
See application file for complete search history.

(56) References Cited

U.S. PATENT DOCUMENTS

2004/0209832 A1* 10/2004 McSwiggen et al. ........... 514/44
2009/0233365 A1* 9/2009 Kim et al. ..................... 435/455

OTHER PUBLICATIONS

Choi et al. Journal of Controlled Release 99 (2004) 445-456.*
Lin et al. Bioconjugate Chemistry 18 (2007) 138-145.*
Tae-Il Kim, Mei Ou, Minhyung Lee, Sung Wan Kim, Arginine-grafted bioreducible poly(disulfide amine) for gene delivery systems, Biomaterials 30 (2009) 568-664.
Sung Wan Kim, Ji Hoon Jeong, Tae-Il Kim, Sung Wan Kim, David A. Bull, VEGF siRNA Delivery System Using Arginine-Grafted Bioreducible Poly(disulfide amine), American Chemical Society, Molecular Pharmaceutics, Dec. 4, 2008, http://pubs.acs.org.

* cited by examiner

*Primary Examiner* — Doug Schultz
(74) *Attorney, Agent, or Firm* — Clayton, Howarth & Cannon, P.C.

(57) ABSTRACT

An arginine-grafted bioreducible poly(disulfide amine) ("ABP") as a reagent for efficient and nontoxic gene delivery is described. ABP forms positively charged nano-particles of less than 200 nm with siRNA. ABP is biodegraded under reducing conditions, such as in the cytoplasm. ABP exhibits much higher transfection efficiency than polyethyleneimine in mammalian cells and exhibits no cytotoxicity. ABP is an effective delivery vehicle for gene silencing with siRNA and may be used for treating cancer.

6 Claims, 30 Drawing Sheets

ARGININE-CONJUGATED BIOREDUCIBLE POLY(DISULFIDE AMINE) POLYMERS FOR GENE DELIVERY SYSTEM

CROSS-REFERENCE TO RELATED APPLICATIONS

This application is a continuation-in-part of U.S. patent application Ser. No. 12/370,515, filed Feb. 12, 2009, which claims the benefit of U.S. Provisional Application No. 61/028,131, filed Feb. 12, 2008, both of which are hereby incorporated by reference in their entireties.

STATEMENT REGARDING FEDERALLY SPONSORED RESEARCH OR DEVELOPMENT

This invention was made with government support under grant no. DK077703 from the National Institutes of Health. The government has certain rights in the invention.

BACKGROUND OF THE INVENTION

This invention relates to non-viral gene delivery carriers. More particularly, this invention relates to arginine-conjugated bioreducible poly(disulfide amine) polymers as gene delivery carriers.

Development of non-toxic and efficient gene delivery carriers is one of the most important requirements for gene therapy. So far, numbers of non-viral gene delivery carriers based on lipids and polymers have been developed as alternatives of viral gene delivery carriers. They have advantages such as non-immunogenicity, convenience of handling, and unlimited delivery capacity of genetic materials over viral vectors. J. S. Remy et al., Gene transfer with lipospermines and polyethyleneimines, 30 Adv. Drug Deliv. Rev. 85-95 (1998); F. Liu & L. Huang, Development of non-viral vectors for systemic gene delivery, 78 J. Control. Release 259-266 (2002); D. Luo & W. M. Saltzman, DNA delivery systems, 18 Nat. Biotechnol. 33-37 (2000). Among them, polymeric gene delivery carriers have multi-functional groups modifiable with biofunctional moieties in their backbones. T. G. Park, J. H. Jeong & S. W. Kim, Current status of polymeric gene delivery systems, 58 Adv. Drug Deliv. Rev. 467-486 (2006). Despite the advantages, their applications to human gene therapy have been limited because of their cytotoxicity and unsatisfactory transfection efficiency. S. Y. Wong et al., Polymer systems for gene delivery-past, present, and future, 32 Prog. Polym. Sci. 799-837 (2007).

Thus, while prior non-viral gene delivery systems are known and are generally suitable for their limited purposes, they possess certain inherent deficiencies that detract from their overall utility.

In view of the foregoing, it will be appreciated that providing arginine-conjugated bioreducible poly(disulfide amine) polymers as gene delivery carriers would be a significant advancement in the art.

BRIEF SUMMARY OF THE INVENTION

An illustrative gene delivery carrier according to the present invention comprises an arginine-grafted bioreducible polymer. In another illustrative embodiment, the arginine-grafted bioreducible polymer comprises a poly(disulfide amine) polymer.

In still another illustrative embodiment, the gene delivery carrier is represented by the formula

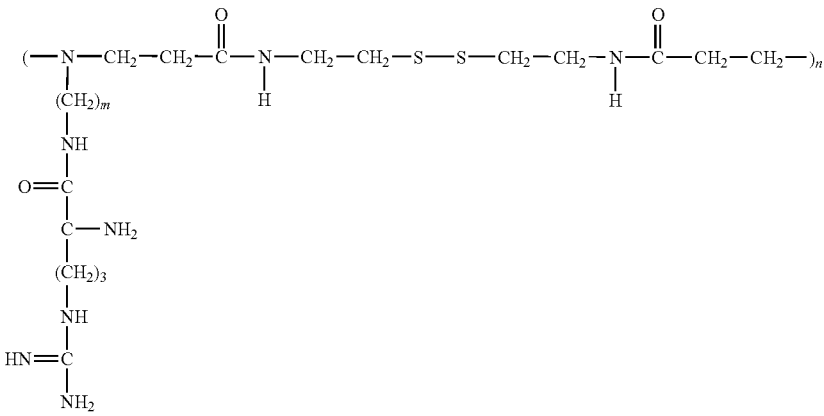

wherein n is about 1 to about 1000 and m is about 1 to about 18. Illustratively, m can be 2, 4, or 6. When m=2, then the arginine-grafted bioreducible polymer can be termed poly(CBA-DAE-R). When m=4, then the arginine-grafted bioreducible polymer can be termed poly(CBA-DAB-R). When m=6, then the arginine-grafted bioreducible polymer can be termed poly(CBA-DAH-R).

Still another illustrative embodiment of the invention comprises a complex comprising a selected nucleic acid bonded to an arginine-grafted bioreducible polymer. For example, the arginine-grafted bioreducible polymer can comprise a poly(disulfide amine) polymer. By way of further example, the arginine-grafted bioreducible polymer can be represented by the formula

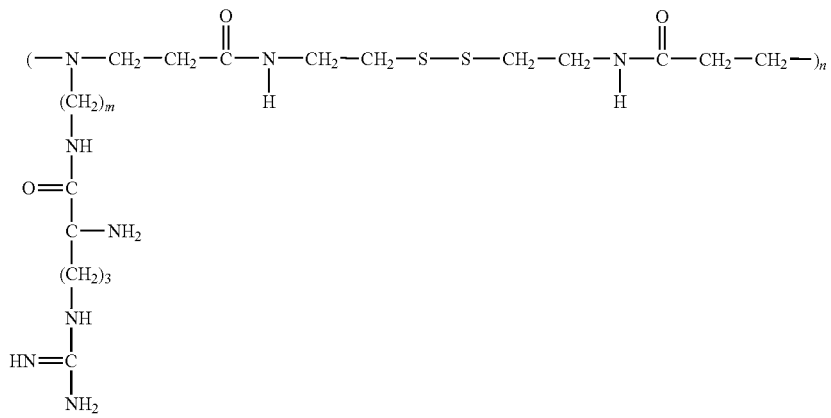

wherein n is about 1 to about 1000 and m is about 1 to about 18. Illustratively, m can be 2, 4, or 6. Illustratively, the selected nucleic acid can comprise a plasmid, siRNA, or an oligonucleotide. Typically, the bonding is due to the anionic nature of the nucleic acid and the cationic nature of the arginine-grafted bioreducible polymer.

In yet another illustrative embodiment of the invention, a method for transfecting mammalian cells comprises contacting selected mammalian cells with a complex comprising a selected nucleic acid bonded to an arginine-grafted bioreducible polymer. For example, the arginine-grafted bioreducible polymer can comprise a poly(disulfide amine) polymer. By way of another example, the arginine-grafted bioreducible polymer can be represented by the formula prises grafting protected arginine residues to a bioreducible polymer and then removing the protecting groups from the grafted arginine residues.

Still another illustrative embodiment of the invention comprises a complex comprising an siRNA bonded to an arginine-grafted bioreducible polymer, wherein the arginine-grafted bioreducible polymer is represented by the formula

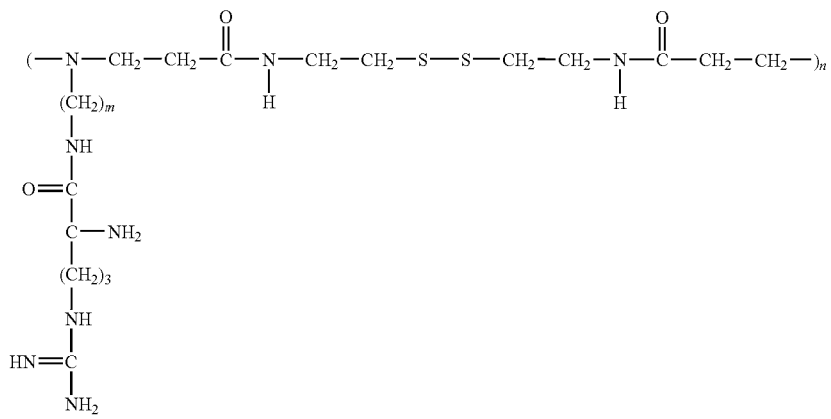

wherein n is about 1 to about 1000 and m is about 1 to about 18. Illustratively, m can be 2, 4, or 6, and the selected nucleic acid can comprise a plasmid, siRNA, or an oligonucleotide.

An illustrative method of making an arginine-conjugated bioreducible polymer according to the present invention com-

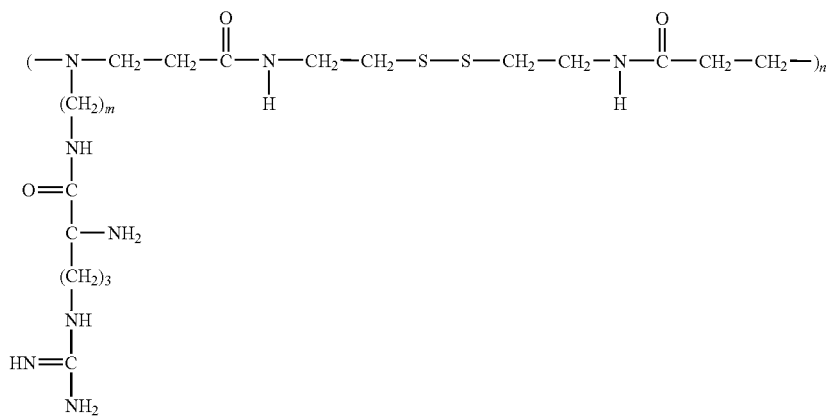

wherein n is about 1 to about 1000 and m is about 1 to about 18. Illustratively m is 2, 4, or 6. The siRNA may be targeted to, for example, vascular endothelial growth factor (VEGF). VEGF siRNA may have a nucleotide sequence as in SEQ ID NO:1 or SEQ ID NO:2.

Yet another illustrative embodiment of the invention comprises a method for treating cancer, the method comprising administering a complex to a patient in need of such treatment such that the complex contacts cancer cells, the complex comprising an siRNA targeted to vascular endothelial growth factor bonded to an arginine-grafted bioreducible polymer represented by the formula Another illustrative embodiment of the present invention comprises a method of silencing a selected gene, the method comprising transfecting a cell capable of expressing the selected gene with a complex comprising an siRNA targeted to the selected gene bonded to an arginine-grafted bioreducible polymer represented by the formula

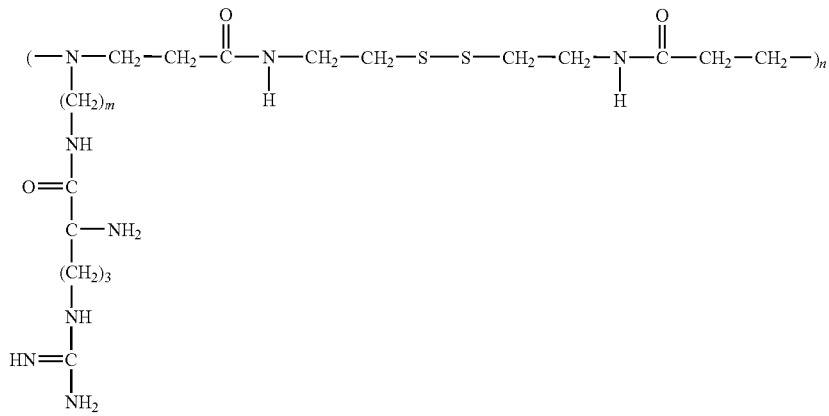

wherein n is about 1 to about 1000 and m is about 1 to about 18. Illustratively, m may be 2, 4, or 6, and the siRNA may have a nucleotide sequence as in SEQ ID NO:1 or SEQ ID NO:2.

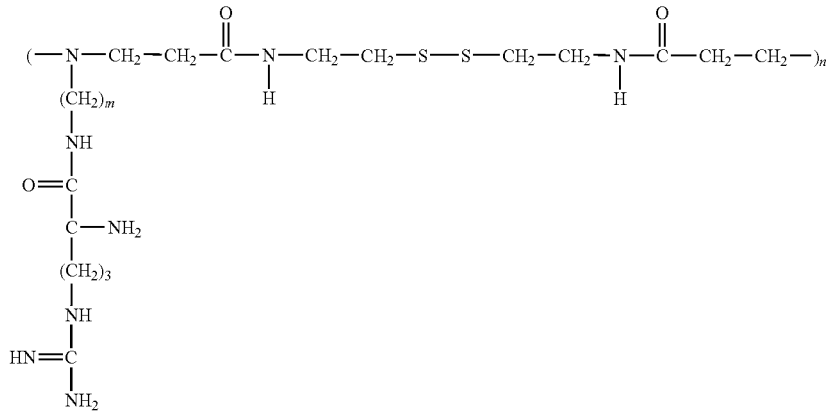

wherein n is about 1 to about 1000 and m is about 1 to about 18. Illustratively, m may be 2, 4, or 6. The selected gene may be, for example, a vascular endothelial growth factor gene, wherein the siRNA may have a nucleotide sequence as in SEQ ID NO:1 or SEQ ID NO:2.

BRIEF DESCRIPTION OF THE SEVERAL VIEWS OF THE DRAWINGS

FIG. 2C shows results obtained with pDNA/poly(CBA-DAH) polyplexes in the presence of 2.5 mM DTT. Lanes C are controls containing only pDNA, and the reference numerals for other lanes indicate weight ratios of poly(CBA-DAH-R) (FIGS. 2A-B) or poly(CBA-DAH) (FIG. 2C) to pDNA.

FIG. 11A shows hydrodynamic diameters and the polyplexes at various weight ratios of polymer to siRNA. FIGS. 11B-E show representative size distribution diagrams and zeta potentials of siRNA/poly(CBA-DAH-R) (FIGS. 11B&C) and siRNA/bPEI (FIGS. 11D&E) polyplexes at weight ratios of 40:1 and 1:1, respectively. The polyplexes were treated with 2.5 mM DTT (FIGS. 11C&E) or without DTT (FIGS. 11B&D).

FIGS. 15A-D show phase contrast and fluorescence overlay, and FIGS. 15E-H shows fluorescence only.

DETAILED DESCRIPTION

Figure 1:
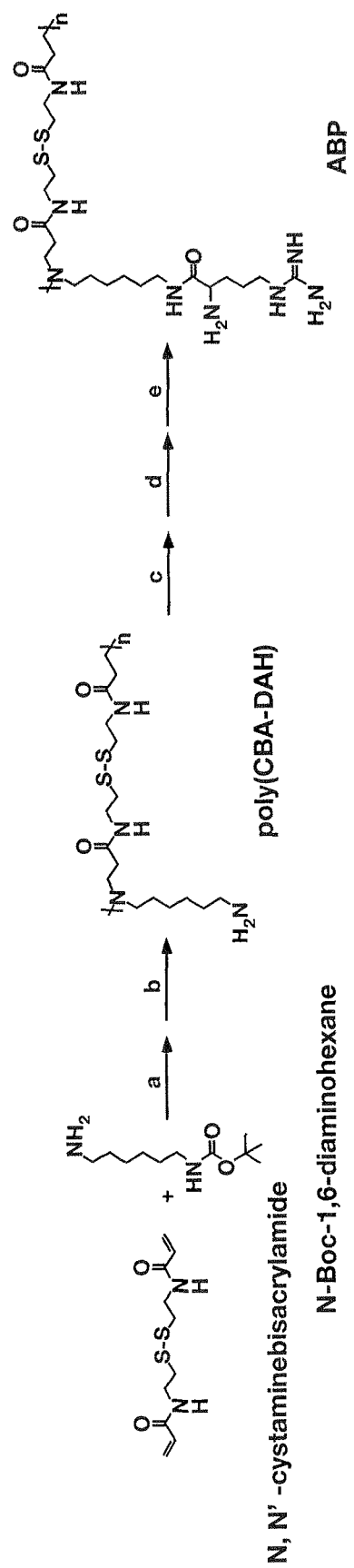
FIG. 1 shows a scheme for synthesis of an illustrative embodiment of an arginine-conjugated bioreducible poly (disulfide amine) polymer ("ABP"), specifically poly(CBA-DAH-R), according to the present invention.

Before the present arginine-conjugated bioreducible poly (disulfide amine) polymers, complexes, and methods are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise.

Unless defined otherwise, all technical and scientific terms used herein have the same meanings as commonly understood by one of ordinary skill in the art to which this invention belongs.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of." As used herein, "consisting of" and grammatical equivalents thereof exclude any element, step, or ingredient not specified in the claim. As used herein, "consisting essentially of" and grammatical equivalents thereof limit the scope of a claim to the specified materials or steps and those that do not materially affect the basic and novel characteristic or characteristics of the claimed invention.

As used herein, "poly(CBA-DAH)" means polymers formed between cystaminebisacrylamide ("CBA") and 1,6-diaminohexane ("DAH"). Similarly, "poly(CBA-DAB)" means polymers formed between CBA and 1,4-diaminobutane ("DAB"), and "poly(CBA-DAE)" means polymers formed between CBA and 1,2-diaminoethane ("DAE").

As used herein, "siRNA" means small interfering RNA, and "RNAi" means RNA interference.

As used herein, "PEI" means polyethylenimine, "PEI25k" means polyethylenimine having a nominal molecular weight of about 25,000, and "bPEI" means branched polyethylenimine.

As used herein, "administering" and similar terms mean delivering a complex to the individual being treated such that the complex is capable of being circulated systemically to the parts of the body where the complex can contact and be internalized in cancer cells. Thus, the complex is typically administered to the individual by systemic administration, typically by subcutaneous, intramuscular, or intravenous administration, or intraperitoneal administration. Injectables for such use can be prepared in conventional forms, either as a liquid solution or suspension or in a solid form suitable for preparation as a solution or suspension in a liquid prior to injection, or as an emulsion. Suitable excipients include, for example, water, saline, dextrose, glycerol, ethanol, and the like; and if desired, minor amounts of auxiliary substances such as wetting or emulsifying agents, buffers, and the like can be added.

Arginine-grafted bioreducible poly(CBA-diaminoalkane) ("ABP") polymers were synthesized for use as reagents for non-viral gene delivery. An illustrative example of ABP is poly(CBA-DAH-R). ABP formed positively charged nanoparticles (less than 200 nm) with pDNA, which are biodegradable in a reducing environment, such as the cytoplasm. The biodegradation of ABP by reductive cleavage can facilitate the efficient release of pDNA from polyplexes and reduce its cytotoxicity, which was found to be very low. ABP showed much higher transfection efficiency than polyethylenimine ("PEI25k") and the backbone polymer (e.g., CBA-DAH) in mammalian cells. In the presence of serum, transfection efficiency of ABP was not reduced much, unlike PEI25k, suggesting that ABP can be also used as an efficient gene delivery carrier for in vivo systems. The transfection efficiency of ABP was not improved by chloroquine treatment, and the cellular uptake pattern of ABP/pDNA polyplexes showed no significant difference from that of poly(CBA-DAH). These results suggest that ABP can act as an endosome buffer and that the greatly enhanced transfection efficiency of ABP is not due to its high cellular penetrating ability but may be mediated by other factors, such as good nuclear localization ability. Therefore, arginine-conjugation to a linear polymer appeared to be very effective, and ABP is an efficient and nontoxic carrier for gene delivery systems.

Synthetic siRNAs 21-23 nucleotides in length mediate target gene silencing by promoting mRNA degradation in the cytoplasm. S. M. Hammond et al., Post-transcriptional gene silencing by double-stranded RNA, 2 Nat. Rev. Genet. 110-119 (2001). Since many diseases are caused by the inappropriate expression of disease-related genes, siRNA technology may provide new therapies for the treatment of diverse human diseases. M. T. McManus et al., Gene silencing in mammals by small interfering RNAs, 3 Nat. Rev. Genet. 737-747 (2002); Y. Dorsett & T. Tuschl, siRNAs: applications in functional genomics and potential as therapeutics, 3 Nat. Rev. Drug Discovery 318-329 (2004). Therapeutics using siRNA offer advantages over conventional pharmaceutics because of their powerful and specific gene silencing ability. The practical applications of siRNAs, however, have been limited by their instability and poor delivery to the necessary site of action. M. Oishi et al., Lactosylated poly(ethylene glycol)-siRNA conjugate through acid-labile beta-thiopropionate linkage to construct pH-sensitive polyion complex micelles achieving enhanced gene silencing in hepatoma cells, 127 J. Am. Chem. Soc. 1624-1625 (2005).

ABP is also an effective siRNA carrier for therapeutic gene silencing of cancer. After intracellular uptake of siRNA/ABP polyplexes, the reductive environment of the cytoplasm cleaves the disulfide linkages in the polymeric backbone, resulting in decomplexing of the siRNA/ABP polyplexes and release of siRNA molecules throughout the cytoplasm. The siRNA/ABP polyplexes, which demonstrate increased membrane permeability with arginine modification, have a similar level of cellular uptake as siRNA/bPEI polyplexes. VEGF siRNA/ABP polyplexes, however, inhibit VEGF expression to a greater degree than VEGF siRNA/bPEI in various human cancer cell lines. The improved RNAi activity demonstrated by the VEGF siRNA/ABP polyplexes is due to enhanced intracellular delivery and effective localization to the cytoplasm of the VEGF siRNAs.

EXAMPLES

Materials

Hyperbranched poly(ethylenimine) (bPEI, 25 kDa), tert-Butyl-N-(6-aminohexyl)carbamate (N-Boc-1,6-diaminohexane, N-Boc-DAH), trifluoroacetic acid (TFA), triisopropylsilane, triisobutylsilane, dithiothreitol (DTT), N,N-diisopropylethylamine (DIPEA), piperidine, 3-[4,5-dimethylthiazol-2-yl]-2,5-diphenyltetrazolium bromide (MTT), chloroquine diphosphate salt, trypan blue solution (0.4%), and DL-buthionine-sulfoxamine (BSO) were purchased from Sigma-Aldrich (St. Louis, Mo.). N,N'-cystaminebisacrylamide (CBA) was purchased from Poly-Sciences, Inc. (Warrington, Pa.). 2-(1H-benzotriazole-1-yl) 1,1,3,3-tetramethyluronium hexafluorophosphate (HBTU) was purchased from Novabiochem (San Diego, Calif.). Fmoc-L-Arg(pbf)-OH was purchased from Anaspec, Inc. (San Jose, Calif.). The plasmid pCMV-Luc, containing a firefly luciferase reporter gene was amplified in $E.\ coli$ DH5α and isolated with a Maxiprep kit (Invitrogen, Carlsbad, Calif.). Luciferase assay system and reporter lysis buffer were purchased from Promega (Madison, Wis.). All cell culture products, including fetal bovine serum (FBS), Dulbecco's phosphate buffered saline (DPBS), Dulbecco's modified Eagle's medium (DMEM), and Roswell Park Memorial Institute 1640 medium (RPMI 1640) were purchased from Invitrogen (Gibco BRL, Carlsbad, Calif.). BCA™ protein assay kit was purchased from Pierce (Rockford, Ill.). YOYO-1 iodide (1 mM solution in DMSO) was purchased from Molecular Probes (Eugene, Oreg.). Human VEGF siRNA sense strand (SEQ ID NO:1) and antisense strand (SEQ ID NO:2) and Green Fluorescent Protein (GFP) siRNA sense strand (SEQ ID NO:3) and antisense strand (SEQ ID NO:4) were synthesized, modified, and purified by Dharmacon Co., Lafayette, Colo.). For flow cytometry and confocal microscopy, siRNA was labeled with Cy3 dye at the 3'-terminal end of the sense strand. All other chemicals were purchased and used without any further purification.

Example 1

Synthesis and Characterization of Poly(CBA-DAH-R)

An illustrative arginine-grafted bioreducible poly(disulfide amine) (ABP), i.e., poly(CBA-DAH-R), was synthesized using poly(CBA-DAH) as a backbone polymer. Poly(CBA-DAH) was selected as a bioreducible backbone polymer because it has modifiable amine groups and showed high transfection efficiency in various cell lines. M. Ou, X. L. Wang, R. Xu, C. W. Chang, D. A. Bull & S. W. Kim, Novel biodegradable poly(disulfide amine)s for gene delivery with high efficiency and low cytotoxicity, 19 Bioconjug. Chem. 626-633 (2008). Briefly, poly(CBA-DAH) was synthesized using N-Boc-DAH and CBA as repeated monomers. Then, 4 equivalents of Fmoc-Arg(pbf)-OH and HBTU, and 8 equivalents of DIPEA were used for arginine-graft reaction of poly (CBA-DAH) in DMF. Then, protecting groups of arginines were removed. FIG. 1 shows the synthetic scheme of this ABP.

In more detail, the backbone poly(disulfide amine) polymer, poly(CBA-DAH) was synthesized by Michael reaction of equivalent moles of N-Boc-DAH and CBA in MeOH/$H_2O$ solution (9:1, v/v), according to the method described in U.S. patent application Ser. No. 12/267,015. The polymerization reaction was maintained in the dark under a nitrogen atmosphere at 60° C. for 5 days. Then, 10% mole of N-Boc-DAH was added to the reaction mixture to consume unreacted acrylamide functional groups, and the reaction was further conducted for 2 days. These steps are represented by arrow "a" in FIG. 1. After precipitation with diethyl ether, the Boc groups of the product were removed by the reagent solution (TFA: triisobutylsilane: $H_2O$=95:2.5:2.5, v/v) at ice bath temperature for 30 min. After additional precipitation with diethyl ether, the polymer product was dialyzed against ultra-pure water with dialysis membrane (MWCO=1000, Spectrum Laboratories, Inc., Rancho Dominguez, Calif.), followed by lyophilization to leave poly(CBA-DAH) as a sticky solid. These steps are represented by arrow "b" in FIG. 1.

Then, grafting of arginine onto poly(CBA-DAH) was performed using 4 equivalents of Fmoc-Arg(pbf)-OH and HBTU, and 8 equivalents of DIPEA in DMF at room temperature for 2 days. This step is represented by arrow "c" in FIG. 1. Then, the reaction product was precipitated with an excess of diethyl ether twice to remove unreacted reagents, and mixed with an equal volume of piperidine solution (30% in DMF) at room temperature for 30 min to remove the Fmoc groups of grafted Fmoc-Arg(pbt)-OH. These steps are represented by arrow "d" in FIG. 1. After two additional precipitations with ether, the reagent solution (TFA: triisopropylsilane: $H_2O$=95:2.5:2.5, v/v) was added to the precipitates to deprotect the pbf groups of arginine residues at room temperature for 30 min. After another precipitation with ether, the final product, poly(CBA-DAH-R) was dialyzed against ultra-pure water overnight and lyophilized before use for analysis and assay. These steps are represented by arrow "e" in FIG. 1.

The synthesis of poly(CBA-DAH-R) was confirmed by $^1H$ NMR (400 MHZ, D20), as follows.

Poly(CBA-DAH-R); $^1H$ NMR ($D_2O$): δ ($NCH_2CH_2CH_2CH_2CH_2CH_2NHCO$)=1.24, δ ($NCH_2CH_2CH_2CH_2CH_2CH_2NHCO$, arginine ($NH_2CHCH_2CH_2CH_2NH$))=1.41-1.53, δ arginine ($NH_2CHCH_2CH_2CH_2NH$)=1.72, δ ($NCH_2CH_2CONH$) =2.59, δ ($CH_2SSCH_2$)=2.74, δ ($NCH_2CH_2CH_2CH_2CH_2CH_2NHCO$)=2.88, δ ($NCH_2CH_2CONH$, $NCH_2CH_2CH_2CH_2CH_2CH_2NHCO$, arginine ($NH_2CHCH_2CH_2CH_2NH$))=3.10-3.18, δ ($NCH_2CH_2CONHCH_2$)=3.41, δ arginine ($NH_2CHCH_2CH_2CH_2NH$) =3.71.

It was found from the calculation of ratio between the integration of arginine proton peaks and the integration of poly(CBA-DAH) proton peaks that almost 100% of the primary amines of poly(CBA-DAH) were modified with arginine residues.

The molecular weight of poly(CBA-DAH-P) was estimated by size-exclusion chromatography (SEC) (Superdex 75 column, calibrated with standard poly[N-(2-hydroxypropyl)-methacrylamide] (pHPMA)) using AKTA FPLC system. Poly(CBA-DAH-R) was dissolved at a concentration of 3 mg/mL. Poly(CBA-DAH-R) was eluted with 0.1 M acetate buffer (30% acetonitrile, v/v, pH 5.5). Flow rate was 0.4 mL/min. The Mw of poly(CBA-DAH-R) was estimated to be $4.45 \times 10^3$ Da/mole and its PDI value was 1.49. The Mw of the backbone polymer, poly(CBA-DAH), was reported to be 3.52 kDa/mole in M. Ou et al., supra. With the assumption that 100% primary amines of poly(CBA-DAH-R) were modified with arginines, the experimental Mw value of poly(CBA-DAH-R) was revealed to be lower than the theoretical value. In general, positively charged cationic polymers are known to have a tendency to appear smaller than they really are in SEC because they may interact with the column and, consequently, they are eluted slowly. Therefore, this result may be due to the strong positive charges of poly(CBA-DAH-R). A higher PDI value of poly(CBA-DAH-R) than that of poly(CBA-DAH) (1.13) is also thought to be induced by this interaction.

Example 2

Agarose Gel Electrophoresis of pDNA/poly(CBA-DAH-R) Complexes

Agarose gel electrophoresis was performed to examine pDNA condensing ability of poly(CBA-DAH-R) in the absence or presence of DTT. Poly(CBA-DAH-R) has internal disulfide bonds and it is expected to be degraded in reducing environments such as cytoplasm, which contains 0.110 mm glutathione. DTT is a well-known reducing agent. Poly(CBA-DAH-R) polyplexes were incubated in 2.5 mM DTT for 1 h to investigate the susceptibility to bioreducing intracellular environments of poly(CBA-DAH-R) polyplexes.

Agarose gel electrophoresis was used to examine pDNA condensing ability of poly(CBA-DAH-R). Poly(CBA-DAH-R) polyplexes were prepared in Hepes-buffered saline (10 mm Hepes, 1 mm NaCl, pH 7.4) at various weight ratios ranging from 0.5 to 20. Agarose gel (0.7%, w/v) containing ethidium bromide solution (0.5 μg/mL) was prepared in TAE (Tris-Acetate-EDTA) buffer. After 30 min of incubation at room temperature, the samples were electrophoresed at 100V for 30 min. Identically prepared poly(CBA-DAH-R) polyplexes were incubated in the presence of 2.5 mm DTT for 1 h at room temperature and then electrophoresed. In this case, poly(CBA-DAH) polyplexes were used as controls. The location of pDNA bands was visualized with a UV illuminator (Gel Documentation Systems, Bio-Rad, Hercules, Calif.).

Figure 2A:
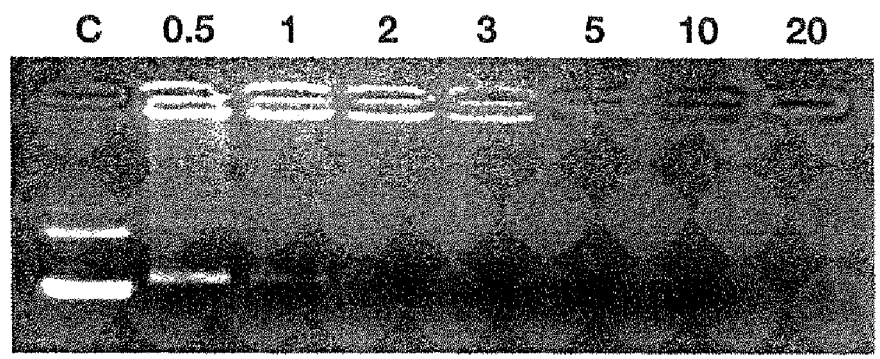
FIGS. 2A-C show results of agarose gel electrophoresis of plasmid DNA ("pDNA") mixed with poly(CBA-DAH-R) in the absence (FIG. 2A) and presence (FIG. 2B) of 2.5 mM dithiothreitol ("DTT").

As shown in FIG. 2A, poly(CBA-DAH-R) can retard pDNA completely from a weight ratio of 2 in the absence of DTT. This result shows that poly(CBA-DAH-R) can condense pDNA well via electrostatic interaction between positive charges of poly(CBA-DAH-R) and negative charges of pDNA phosphates.

Figure 2B:
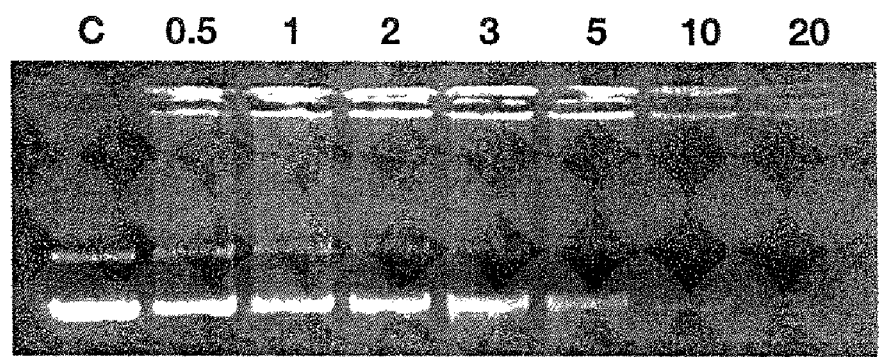

On the other hand, pDNA released from poly(CBA-DAH-R) polyplexes was observed even at a weight ratio of 10 in the presence of 2.5 mm DTT (FIG. 2B). This means that poly(CBA-DAH-R) is degraded in reducing environments and thereafter it cannot condense pDNA because of bioreducible cleavage of internal disulfide bonds. Consequently, it is expected that poly(CBA-DAH-R) polyplexes can release pDNA by bio-reduction in cytoplasm, which may lead to efficient transfection.

Figure 2C:
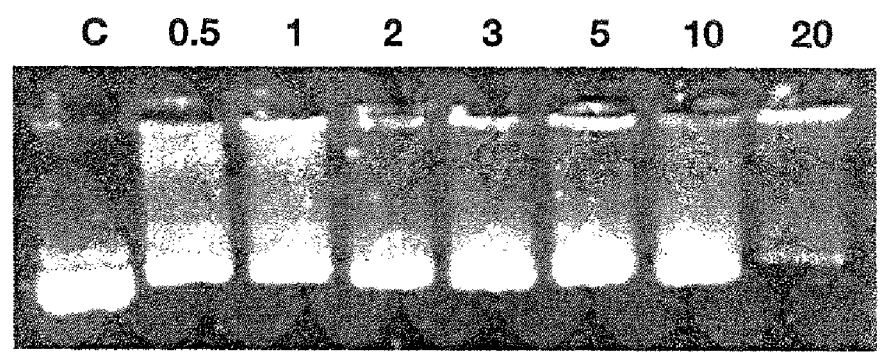

Poly(CBA-DAH-R) was still able to retard pDNA at a weight ratio of 20 even in the presence of DTT. In contrast with poly(CBA-DAH-R), it was observed that poly(CBA-DAH) could not condense pDNA at the same weight ratio in the presence of DTT (FIG. 2C). Higher molar ratios of poly(CBA-DAH) were used in each poly(CBA-DAH)-containing polyplex than those of poly(CBA-DAH-R)-containing polyplexes at the same weight ratio, because the molecular weight of poly(CBA-DAH) is less than that of poly(CBA-DAH-R). From this result, it is thought that poly(CBA-DAH-R) can form more stable polyplexes than poly(CBA-DAH). Considering the structural differences between poly(CBA-DAH-R) and poly(CBA-DAH), it may be that grafted arginine residues help poly(CBA-DAH-R) form stable polyplexes with pDNA due to their strong positive charges. In general, linear biodegradable polymers are degraded into two molecules via just one cleavage of a backbone bond. Their fast degradation rate is believed to result in low levels of gene delivery to the cell nucleus. Therefore, cross-linked biodegradable polymers have been developed to overcome this handicap of linear polymers for efficient gene delivery because one cleavage of a backbone bond does not lead to the break of whole polymer structure in cross-linked polymers. Y.-b. Lim et al., Biodegradable endosome disruptive, and cationic network-type polymer as a highly efficient and nontoxic gene delivery carrier, 13 Bioconjug. Chem. 952-957 (2002); T.-i. Kim et al., Synthesis of biodegradable cross-linked poly(β-amino ester) for gene delivery and its modification, inducing enhanced transfection efficiency and stepwise degradation, 16 Bioconjug. Chem. 1140-1148 (2005). Thus, this lower susceptibility to bio-reduction of poly(CBA-DAH-R) may contribute to its higher transfection efficiency than poly(CBA-DAH), although poly(CBA-DAH-R) is a linear polymer.

Example 3

Average Sizes and Zeta-potential Measurements of pDNA/poly(CBA-DAH-R) Polyplexes The average sizes and Zeta-potentials of pDNA/poly(CBA-DAH-R) polyplexes were measured because polyplexes are thought to need an appropriate size for efficient uptake into cells, and a net positive charge of a polyplex is thought to be helpful for its absorption to negatively charged cellular membrane, also leading to efficient intracellular trafficking. D. W. Pack et al., Design and development of polymers for gene delivery, 4 Nat. Rev. Drug Discov. 581-593 (2005). The backbone polymer, poly(CBA-DAH), was used as a control.

The average sizes of poly(CBA-DAH-R) and poly(CBA-DAH) polyplexes were examined using a Zetasizer 3000 (Malvern Instruments, USA) with a He—Ne Laser beam (633 nm, fixed scattering angle of 90°) at 25° C. Polyplex solutions (10 μg of PDNA in 0.5 mL) were prepared in Hepes buffered saline (10 mm Hepes, 1 mm NaCl, pH 7.4) at various weight ratios ranging from 0.5 to 20. After 30 min of incubation, polyplex solutions were diluted to a final volume of 4 mL before measurement. Measured sizes were presented as the average values of 5 runs.

Figure 3:
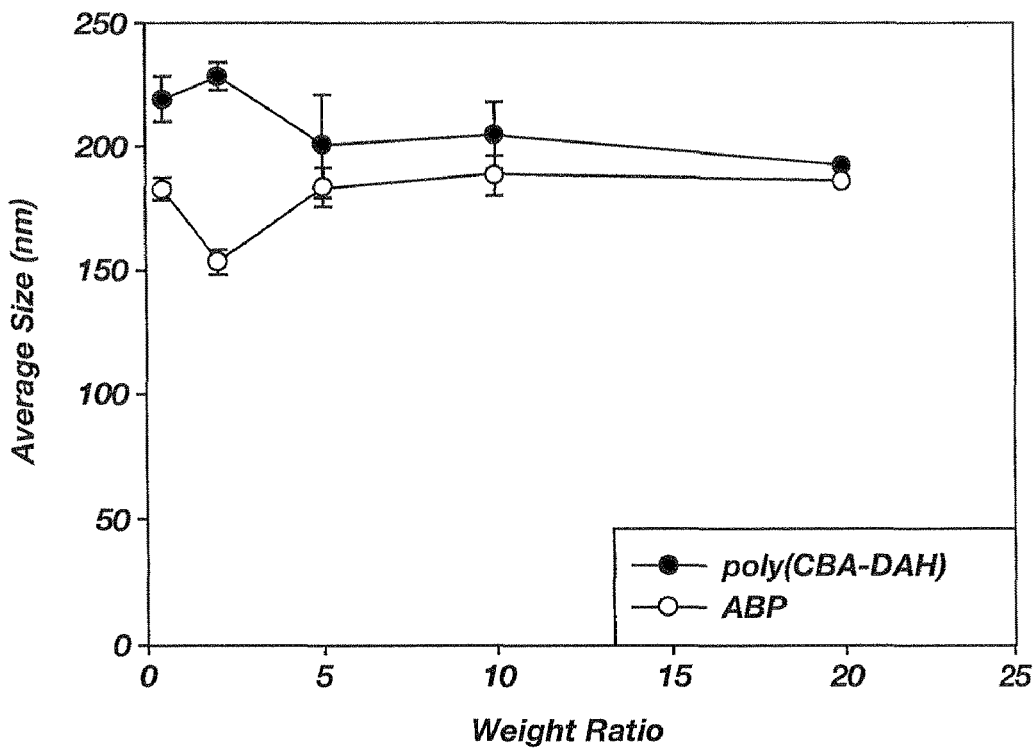
FIGS. 3 and 4 show the average sizes (FIG. 3) and zeta-potential values (FIG. 4) of pDNA/poly(CBA-DAH-R) (○) and pDNA/poly(CBA-DAH) (●) polyplexes.

Poly(CBA-DAH-R) polyplexes displayed average sizes less than 200 nm at all weight ratios used (FIG. 3). Below a weight ratio of 5, some differences were found in average sizes of both polymers but no significant differences over a weight ratio of 5 were observed. This result shows that poly(CBA-DAH-R) can condense pDNA into nano-sized particles appropriate for gene delivery.

Figure 4:
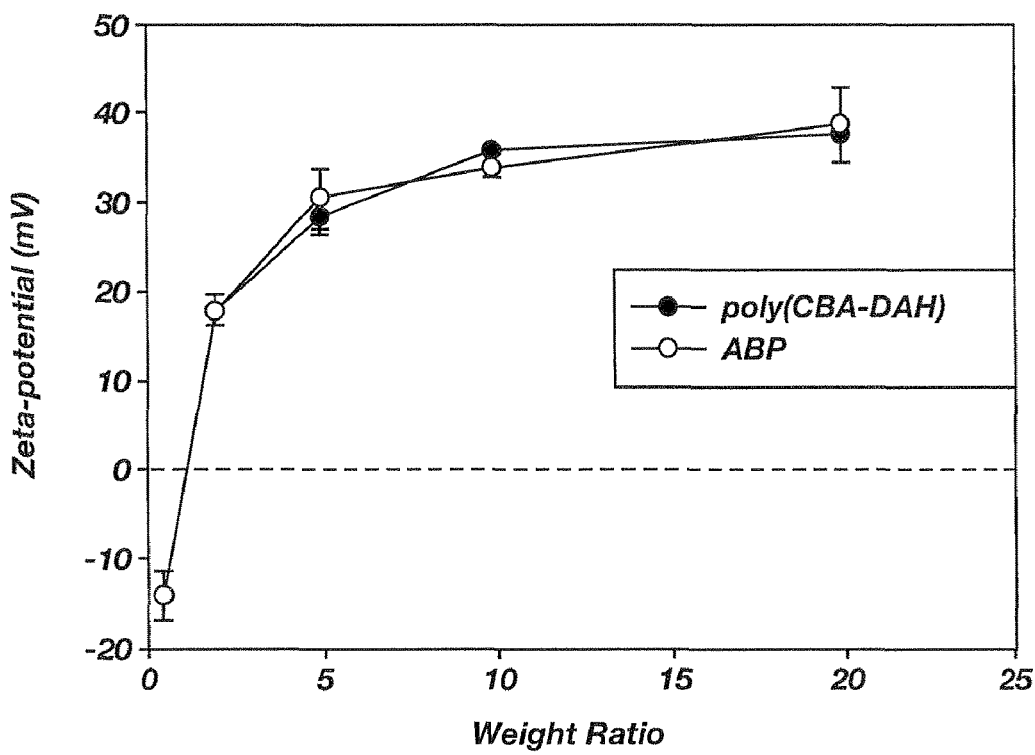

Zeta-potential measurements of polyplexes were also carried out using a Zetasizer 3000 at 25° C. Poly(CBA-DAH-R) and poly(CBA-DAH) polyplexes were prepared by the same method as in the size measurement experiments. Potential values were presented as the average values of 3 runs. As shown in FIG. 4, poly(CBA-DAH-R) polyplex displayed a negative value (−15 mV) at a weight ratio of 1, suggesting that a stable polyplex is not formed at that ratio, which is consistent with the agarose gel electrophoresis results (Example 2). Zeta-potential values of poly(CBA-DAH-R) polyplexes increased gradually according to the increase of polyplex weight ratios, finally reaching positive plateau values (30-40 mV) from a weight ratio of 10. Zeta-potential values of poly (CBA-DAH-R) and poly(CBA-DAH) polyplexes showed no significant differences between them. These results suggest that poly(CBA-DAH-R) forms positively charged polyplexes that can mediated efficient transfection and that the polyarginine grafted onto poly(CBA-DAH) does not affect the size or Zeta-potential values of polyplexes.

Example 4

Cytotoxicity of pDNA/poly(CBA-DAH-R) Polyplexes

MTT assay was performed to examine the cytotoxicity of pDNA/poly(CBA-DAH-R) polyplexes. C2C12 mouse myoblast cells were seeded in a 96-well tissue culture plate at $1\times10^4$ cells/well in 90 μL DMEM medium containing 10% FBS. Cells achieving 70-80% confluence after 24 h were exposed to 10 μL of the polyplex solutions (0.5 μg pDNA) at different weight ratios for 4 h in serum-free DMEM medium. After exchange of medium for fresh DMEM medium containing 10% FBS, the cells were further maintained for 48 h. Then, 25 μL of stock solution of MTT (2 mg/ml in PBS) was added to each well. After 2 h of incubation at 37° C., the medium was removed carefully and 150 μL of DMSO was added to each well to dissolve the formazan crystal formed by proliferating cells. Absorbance was measured at 570 nm using a microplate reader (Model 680, Bio-Rad Lab, Hercules, Calif.) and recorded as a percentage relative to untreated control cells. All experiments were performed in quadruplicate.

Figure 5:
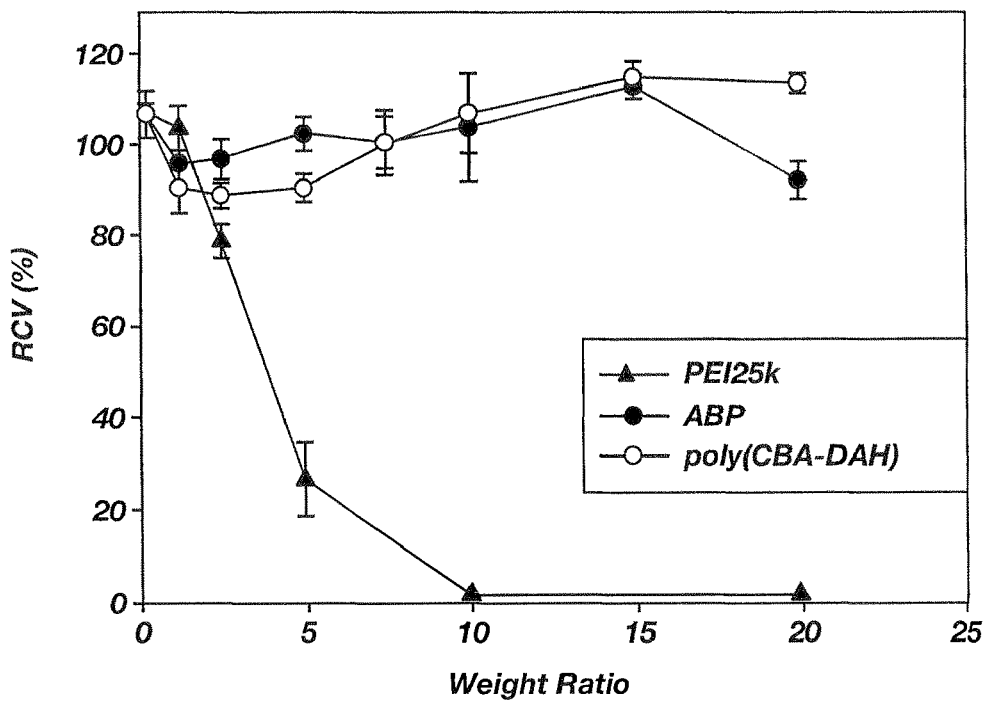
FIG. 5 shows results of cytotoxicity assays of polyplexes in C2C12 cells; data are expressed as relative cell viability ("RCV") as a function of weight ratio of carrier (▲-PEI25k, ●-poly (CBA-DAH-R), ○-poly(CBA-DAH)) to pDNA.

As shown in FIG. 5, pDNA/poly(CBA-DAH-R) polyplexes were observed to exhibit no significant cytotoxicity (RCV>90%) compared to poly(CBA-DAH), even at a weight ratio of 80 in C2C12 cells. The reason for this low cytotoxicity may be that poly(CBA-DAH-R) can be degraded into non-toxic small molecules in cells. The cytotoxicity of PEI25k was found to be very high, as is well-known.

These results suggest that poly(CBA-DAH-R) can be used for gene delivery.

Example 5

In Vitro Transfection of pDNA/poly(CBA-DAH-R) Polyplexes

In vitro transfection experiments of pDNA/poly(CBA-DAH-R) polyplexes were performed using a luciferase reporter gene in C2C12 mouse myoblast cells and NIH3T3 mouse embryonic fibroblasts cells. PEI25k and poly(CBA-DAH) were used as controls. Polyplexes of PEI25k and poly (CBA-DAH) were prepared at weight ratios of 1 and 40, respectively.

More particularly, C2C12 and NIH3T3 cells were seeded at a density of $5\times10^4$ cells/well in a 24-well plate in DMEM medium containing 10% FBS and grown to reach 70-80% confluence prior to transfection. Before transfection, the medium in each well was exchanged for fresh serum-free medium. For transfection in serum, the medium was not exchanged at this time. The cells were treated with polyplex solutions (0.5 μg PDNA) at different weight ratios for 4 h at 37° C. After exchange with fresh medium containing 10% FBS, cells were further incubated for 2 days before assay. Then, the growth medium was removed and the cells were rinsed with DPBS and shaken for 30 min at room temperature in 120 μL of Reporter Lysis Buffer. Luciferase activity was measured by a luminescence assay, and a protein quantification assay was performed using a BCA™ Protein Assay Reagent Kit. The luciferase activity of 25 μL of cell lysate was measured with 100 μL of luciferase assay reagent on a luminometer (Dynex Technologies Inc., Chantilly, Va.). The final results were reported in terms of RLU/mg cellular protein. All experiments were performed in triplicate.

Figure 6:
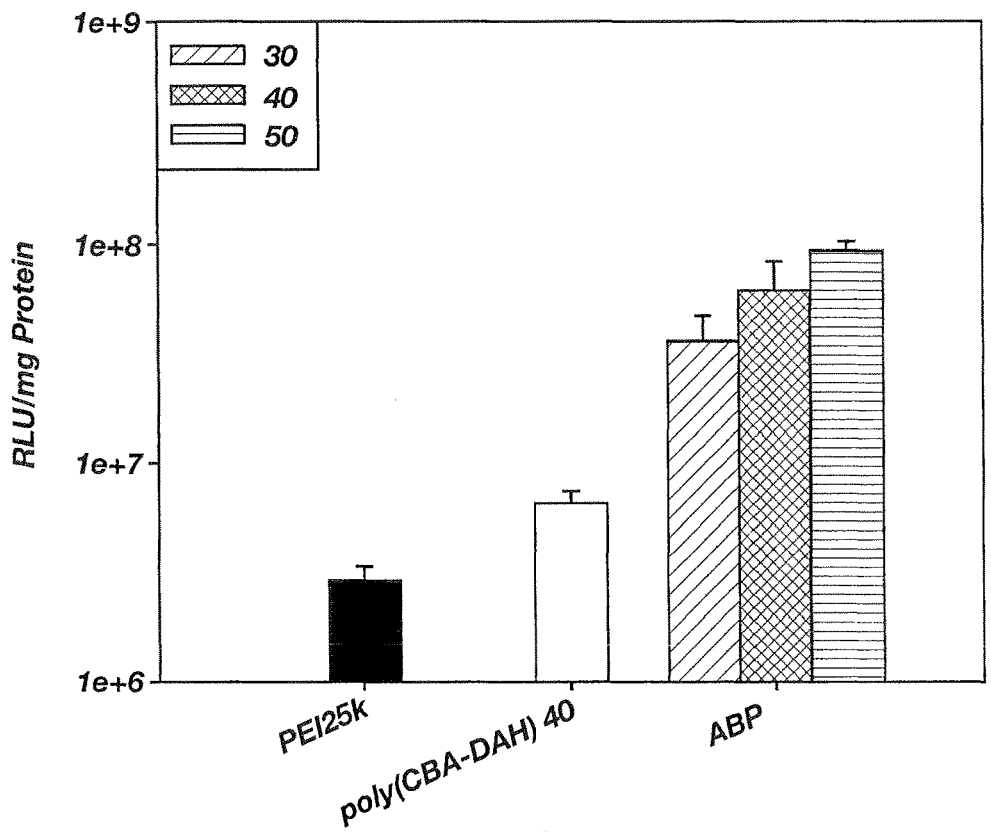
FIGS. 6 and 7 shows the relative transfection efficiencies of a polyethylenimine control (dark bars, "PEI25k"), poly (CBA-DAH) (open bars), and poly(CBA-DAH-R) (hatched bars) as a function of the weight ratio of carrier to pDNA in C2C12 cells (FIG. 6) and NIH3T3 cells (FIG. 7); numbers in the boxes indicate the weight ratios of the pDNA/poly(CBA-DAH-R) polyplexes.
Figure 7:
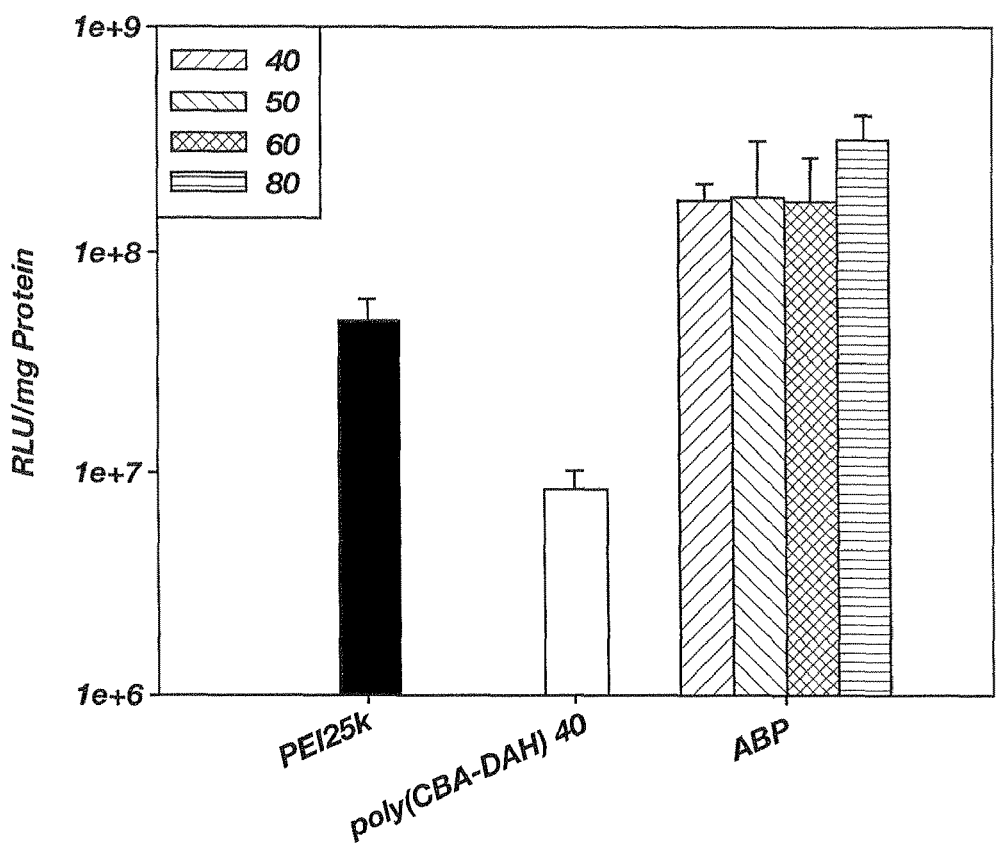

FIG. 6 shows the result in C2C12 cells in the absence of serum. The transfection efficiency of poly(CBA-DAH-R) at a weight ratio of 50 was found to be about 30 times higher than that of PEI25k. ABP displayed about 9 times and 14 times higher transfection efficiency than poly(CBA-DAH) at weight ratios of 40 and 50, respectively. In FIG. 7, poly(CBA-DAH-R) showed about 3-6 times higher transfection efficiency than PEI25k and 20-37 times higher transfection efficiency than poly(CBA-DAH) in NIH3T3 cells in the absence of serum.

Figure 8:
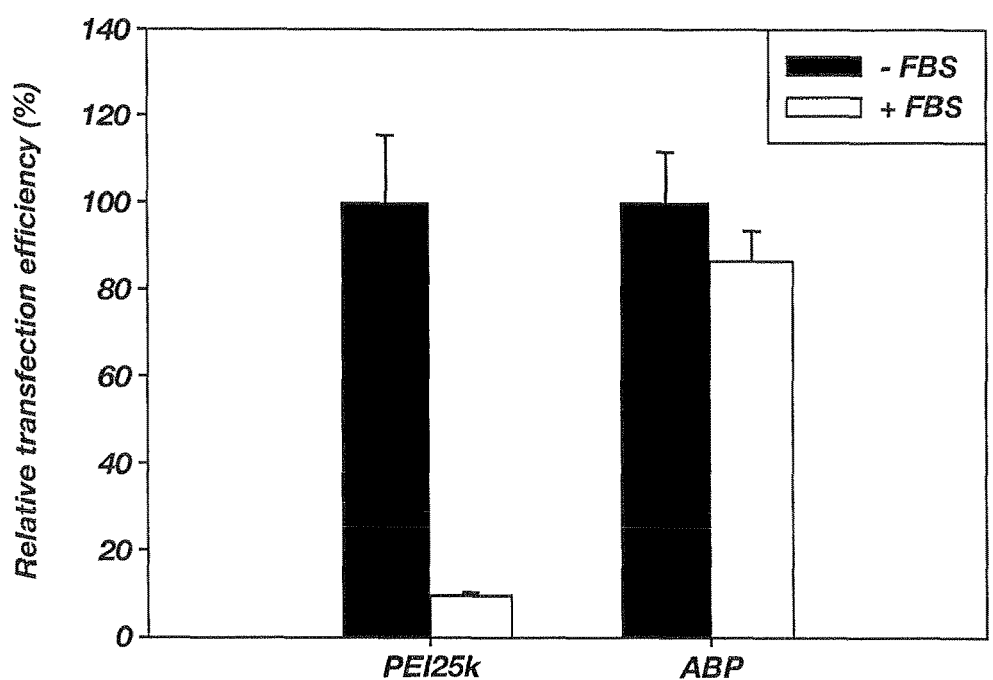
FIG. 8 shows relative transfection efficiency in C2C12 cells of pDNA/PEI25k ("PEI25k") and pDNA/poly(CBA-DAH-R) ("poly(CBA-DAH-R)") polyplexes in the absence (dark bars) and presence (open bars) of fetal bovine serum ("FBS"). Relative transfection efficiency is the ratio, expressed as a percentage, of transfection efficiency with serum to transfection efficiency without serum.

In the presence of serum, the transfection efficiency of poly(CBA-DAH-R) was reduced just 15% in comparison with its efficiency in the absence of serum, although PEI25k showed a 90% reduction in efficiency in C2C12 cells (FIG. 8). This result means that the transfection process of poly(CBA-DAH-R) will not be seriously inhibited from serum interaction and that poly(CBA-DAH-R) has potential as a gene delivery systems in vivo as well as in vitro.

These results also show that arginine grafted to linear poly (CBA-DAH) can greatly increase the transfection efficiency of the polymer.

Example 6

Transfection Mechanisms Study

A series of transfection experiments were performed to examine the transfection mechanism of pDNA/poly(CBA-DAH-R) polyplexes. First, 100 μM chloroquine was added to the cells before treatment of polyplexes and the cells were further incubated for 4 h during transfection. Chloroquine is a well-known endosome disrupting agent which can facilitate the release of polyplexes from endosome and lead to enhanced transfection. K. Ciftci & R. J. Levy, Enhanced plasmid DNA transfection with lysosomotropic agents in cultured fibroblasts, 218 Int. J. Pharm. 81-92 (2001). PEI25k was used as a control.

More particularly, transfection experiments were performed with or without chloroquine to examine the cellular uptake mechanism of poly(CBA-DAH-R) polyplexes. C2C12 cells were seeded at a density of $5\times10^4$ cells/well in a 24-well plate in DMEM medium containing 10% FBS and grown to reach 70-80% confluence prior to transfection. Each polyplex was prepared with 0.5 μg of pDNA at a fixed weight ratio (PEI: 1, poly(CBA-DAH-R): 40). Then, the cells were treated with 100 μM chloroquine before transfection, and the cells were incubated in the presence or absence of chloroquine during transfection. After 4 h of incubation, all the cells were washed with DPBS and maintained in DMEM containing 10% FBS at 37° C. for 2 days. Further experiments and assays were performed by the same transfection method mentioned above in the absence of serum. All experiments were performed in triplicate.

Figure 9:
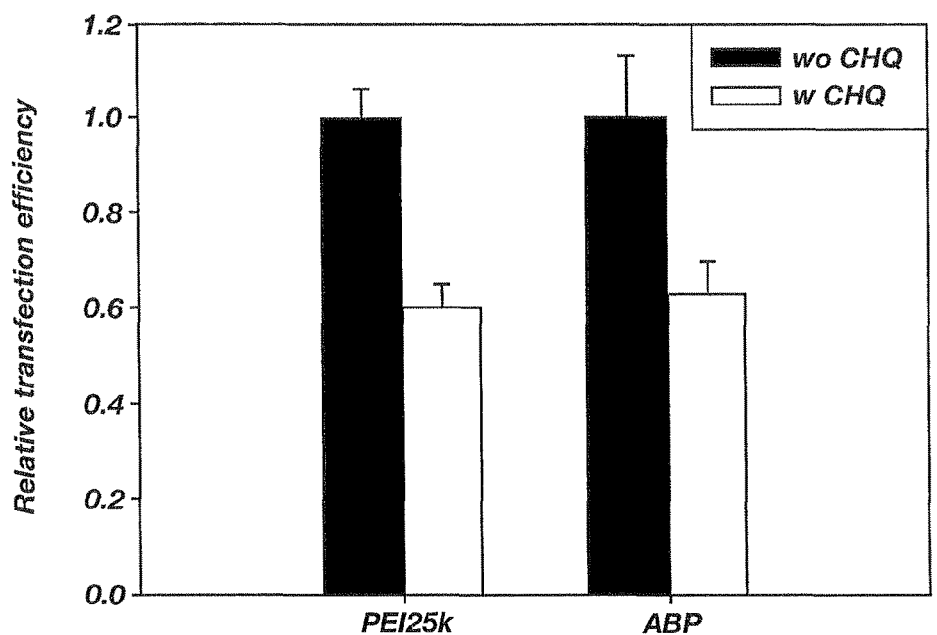
FIG. 9 shows relative transfection efficiency in C2C12 cells of PDNA/PEI25k ("PEI25k") and pDNA/poly(CBA-DAH-R) ("poly(CBA-DAH-R)") polyplexes in the absence (dark bars) and presence (open bars) of 100 μM chloroquine ("CHQ").

As shown in FIG. 9, transfection efficiencies of both pDNA/PEI25k and pDNA/poly(CBA-DAH-R) polyplexes were found to be reduced to about 60% in the presence of chloroquine in comparison with the efficiencies in the absence of chloroquine. This result shows that 100 µM chloroquine does not improve the transfection of these polymers. PEI25k has various internal amines that can act as endosome buffers, and a slight decrease of transfection efficiency of PEI25k in treatment of chloroquine has been already reported. A. Akinc et al., Exploring polyethylenimine mediated DNA transfection and the proton sponge hypothesis, 7 J. Gene Med. 657-663 (2005). It was also suggested that the backbone polymer of poly(CBA-DAH-R), poly (CBA-DAH), can have endosome buffering moieties. M. Ou et al., supra. Therefore, it is thought that poly(CBA-DAH-R) can function as an endosome buffer itself. However, this result does not explain the greatly enhanced transfection of poly (CBA-DAH-R) in comparison with poly(CBA-DAH).

Next, the cellular uptake of polyplexes was investigated by flow cytometry. YOYO-1 iodide-labeled PDNA was used for fluorescence measurements and poly(CBA-DAH) was used as a control polymer. After treatment of polyplexes, the cells were incubated in 0.4% trypan blue solution for 5 min to quench the fluorescence of extra-cellular polyplexes.

C2C12 cells were seeded at a density of $2 \times 10^5$ cells/well in a 6-well plate in DMEM medium containing 10% FBS and grown to reach 70-80% confluence prior to transfection. Before transfection, the medium in each well was exchanged for fresh serum-free medium. Plasmid DNA was labeled with YOYO-1 iodide (1 molecule of the dye per 100 base pairs of the nucleotide). M. Ogris et al., A versatile assay to study cellular uptake of gene transfer complexes by flow cytometry, 1474 Biochim. Biophys. Acta 237-143 (2000). The cells were treated with polyplex solutions (1 µg PDNA) at different weight ratios for 4 h at 37° C. Then, medium was aspirated from the wells, and the cells were washed two times with ice-cold DPBS. To quench the fluorescence of polyplexes adsorbed on the cell surface, the cells were incubated with 0.4% trypan blue solution for 5 min and washed with DPBS again. S. Sahlin et al., Differentiation between attached and ingested immune complexes by a fluorescence quenching cytofluorometric assay, 60 J. Immunol. Methods 115-124 (1983). After trypsinization, the cells were collected by centrifuge at 1500 rpm and suspended in 1 mL DPBS.

The cellular uptake of fluorescence-labeled polyplexes were examined using the BD FACScan analyzer (Becton Dickinson, San Jose, Calif.) at a minimum of $1 \times 10^4$ cells gated per sample. Analysis was performed by using Becton Dickinson CellQuest software.

Figure 10:
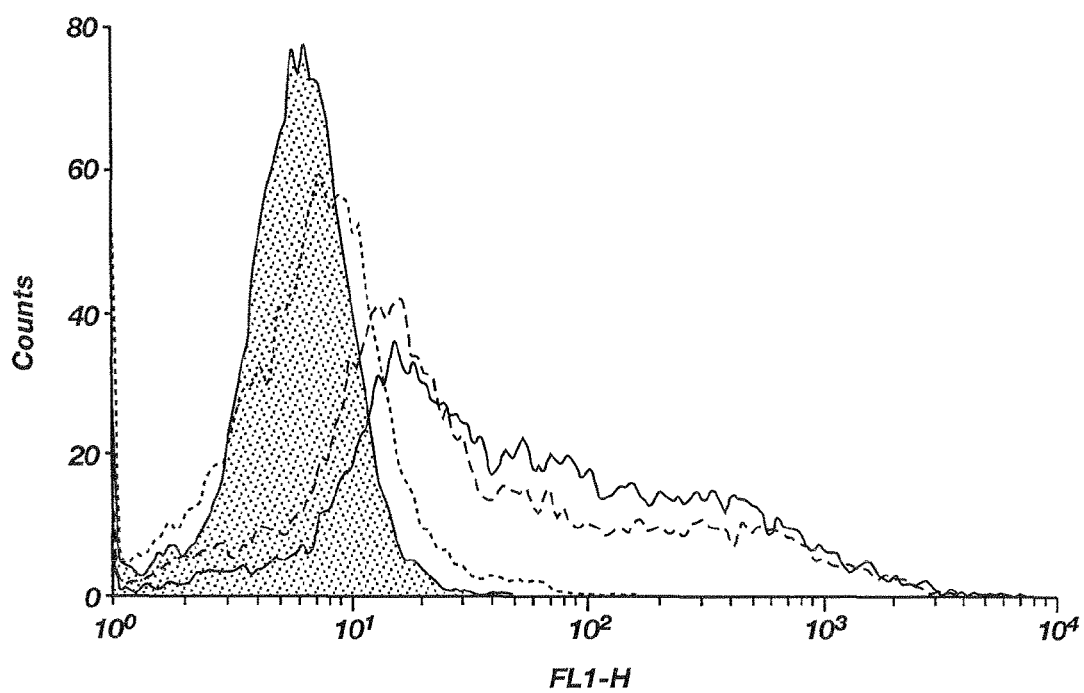
FIG. 10 shows cellular uptake results in C2C12 cells as measured by flow cytometry where the shaded peak shows cells only, the dotted line shows pDNA only, the dashed line shows pDNA/poly(CBA-DAH) polyplexes, and the solid bold line shows pDNA/ABP polyplexes.

As shown in FIG. 10, there seems to be no significant difference of fluorescence peaks between the pDNA/poly (CBA-DAH) and pDNA/poly(CBA-DAH-R) polyplexes despite their structural differences. This result means that conjugated arginine residues do not have any significant functions for cellular uptake of poly(CBA-DAH-R) polyplexes. Therefore, it is interpreted that greatly enhanced transfection efficiency of poly(CBA-DAH-R) is not induced by its high cellular penetrating ability, but may be mediated by other factors such as good nuclear localization ability.

Example 7

In this example, the procedure of Example 1 is followed except that tert-butyl N-(2-aminoethyl)carbamate (N-Boc-1, 2-diaminoethane, N-Boc-DAE) is substituted for tert-butyl-N-(6-aminohexyl)carbamate (N-Boc-1,6-diaminohexane, N-Boc-DAH).

Example 8

In this example, the procedure of Example 1 is followed except that tert-butyl N-(4-aminobutyl)carbamate (-Boc-1,4-diaminobutane, N-Boc-DAB) is substituted for tert-butyl-N-(6-aminohexyl)carbamate (N-Boc-1,6-diaminohexane, N-Boc-DAH).

Example 9

Dynamic Light Scattering Assay of siRNA/poly(CBA-DAH-R) Polyplexes

The formation of siRNA polyplexes and the reductive degradation of poly(CBA-DAH-R) were assessed by dynamic light scattering (DLS) measurements. Polyplexes of siRNA with poly(CBA-DAH-R) and bPEI were formed at various weight ratios (polymer/siRNA) ranging from 10:1 to 60:1 and from 0.1:1 to 60:1, respectively. A fixed amount of siRNA (3 µg) was complexed with different amounts of polymers (poly (CBA-DAH-R) or bPEI) in 0.4 mL HEPES buffer (20 mM HEPES, 5% glucose, pH 7.4). After 30 min incubation at room temperature, the polyplex solution was diluted 6-fold with deionized water. To determine the degradation ability of the siRNA/poly(CBA-DAH-R) polyplexes, siRNA polyplexes that were formed with poly(CBA-DAH-R) and bPEI at weight ratios of 40:1 and 1:1, respectively, were further incubated with 2.5 mM DTT for 2 h at 37° C. Particle sizes and surface charges were measured by DLS using a Zetasizer 3000HS (Malvern Instrument, Inc., Worcestershire, U.K.) at a wavelength of 677 nm with a constant angle of 90° at 25° C.

Figure 11A:
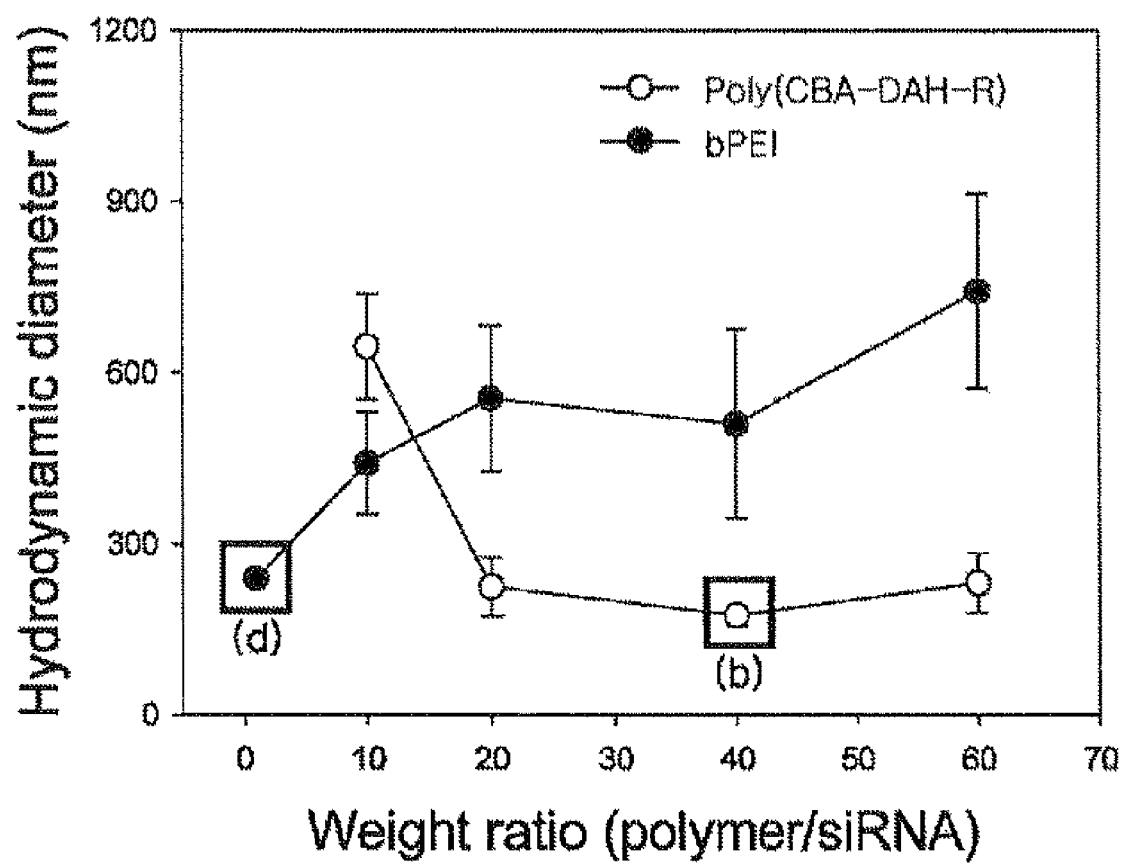
FIGS. 11A-E show particle sizes and surface charges of siRNA/poly(CBA-DAH-R) and siRNA/bPEI polyplexes.
Figure 11B:
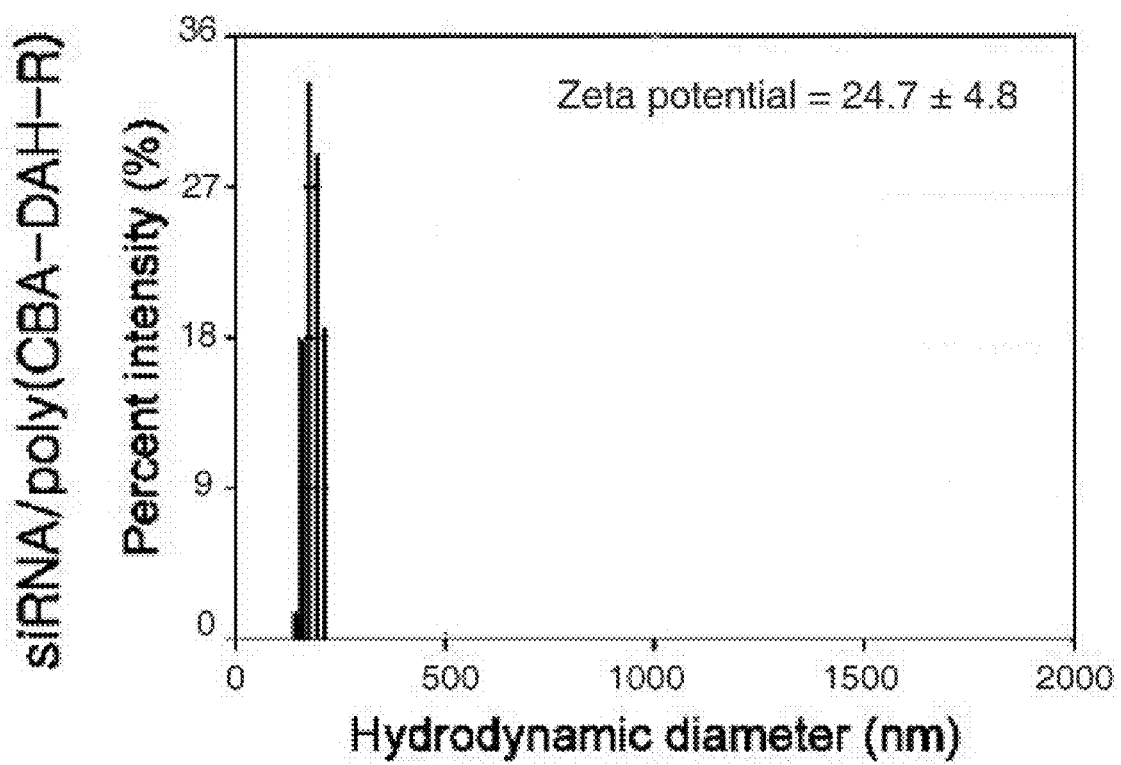
Figure 11C:
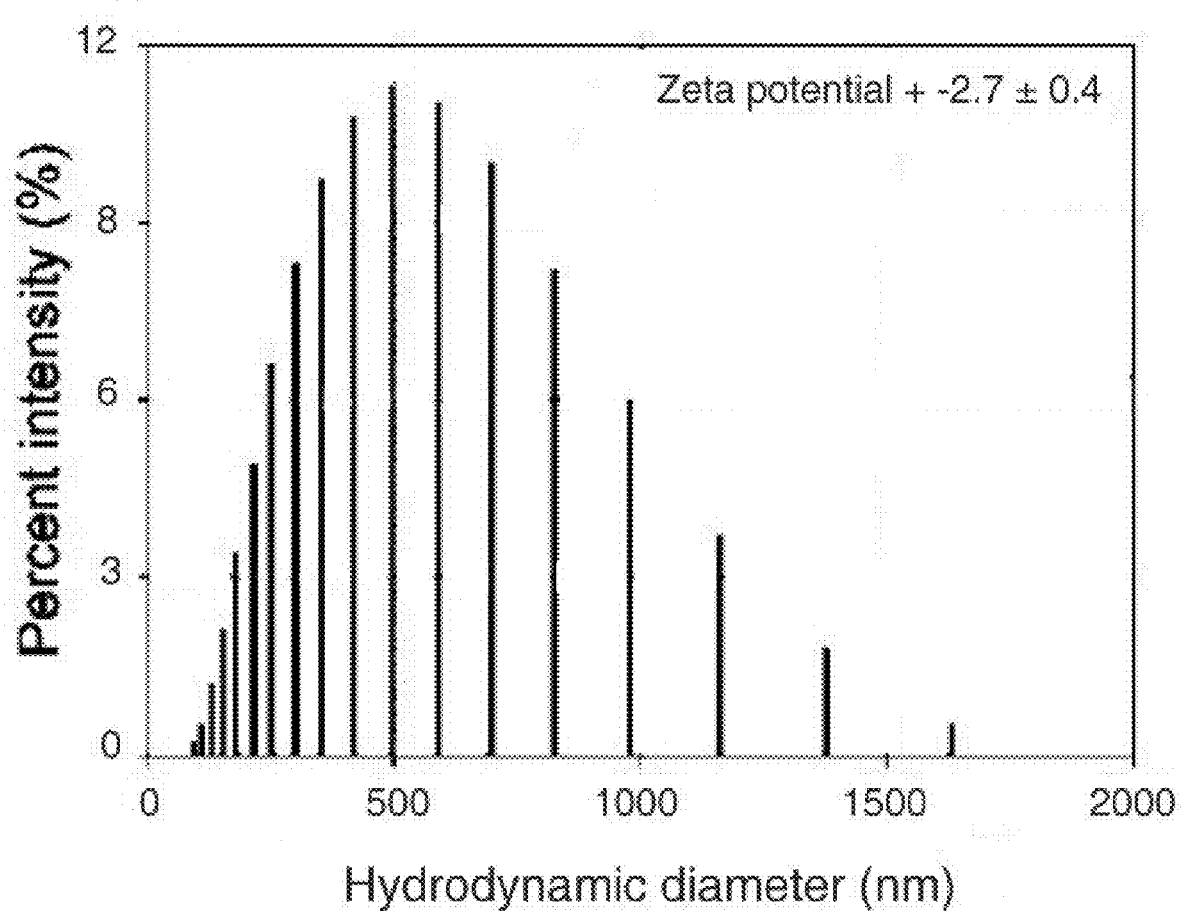
Figure 11D:
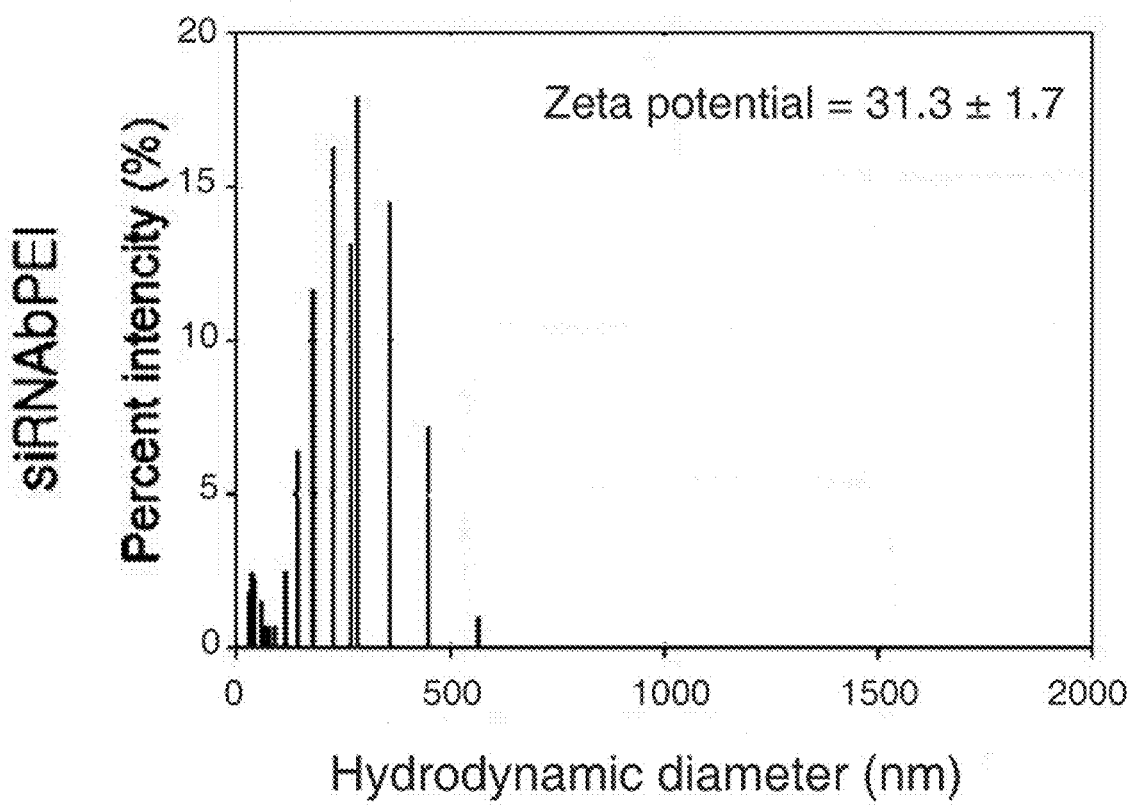
Figure 11E:
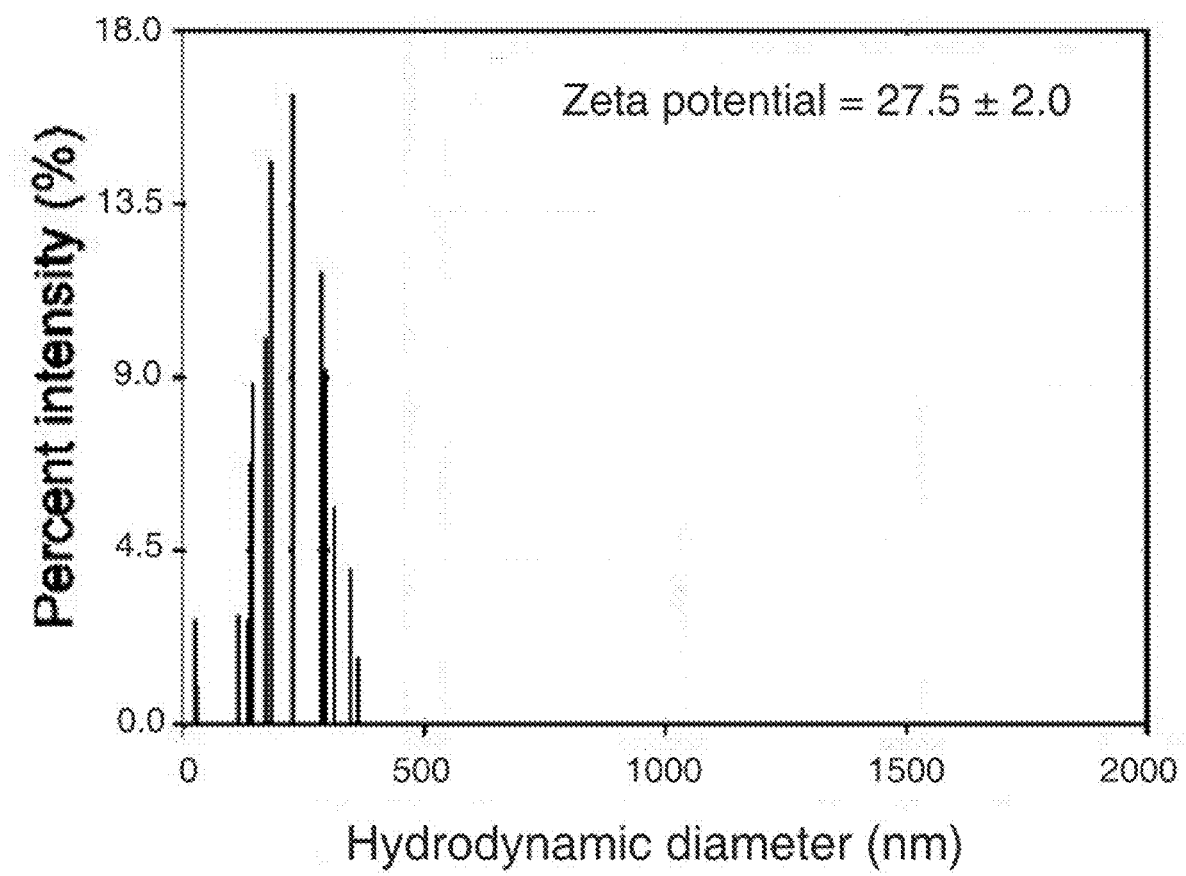

FIG. 11A-E show the hydrodynamic diameters of siRNA/poly(CBA-DAH-R) and siRNA/bPEI polyplexes. Poly (CBA-DAH-R) and bPEI were complexed with siRNA molecules at 200 nm in diameter at weight ratios (polymer/siRNA) of 40:1 and 1:1, respectively. Poly(CBA-DAH-R) started to condense siRNA at a weight ratio of 10:1, though the polyplexes were not stabilized until a weight ratio of 20:1. The siRNA/poly(CBA-DAH-R) polyplexes were stably formed at a few hundred nanometers in size with weight ratios above 20:1. The bioreducible polycation poly(CBA-DAH-R) spontaneously formed stable nanosized polyplexes with siRNA molecules due to the electrostatic interactions between the positively charged side-chain arginine groups of the polymer and the negatively charged phosphate groups of the siRNAs. DLS analysis showed that the particle size of the siRNA/bPEI polyplexes was dramatically increased with an increase in the weight ratio, due to significant particle aggregation of highly positive charged polyplexes (zeta potential over +35 mV). It has been reported that strongly charged particles are rapidly aggregated under physiologic conditions. Y. Wang et al., A facile entrapment approach to construct PEGylated polyplexes for improving stability in physiological conditions, 58 Colloids Surf., B 188-196 (2007). To examine whether the siRNA/poly(CBA-DAH-R) polyplexes degrade and release free siRNAs under reductive conditions, the siRNA polyplexes with poly(CBA-DAH-R) and bPEI were preincubated in 2.5 mM DTT solution and the polyplexes were analyzed by DLS. There was no detectable difference in particle size and surface charge for the siRNA/bPEI polyplexes with and without DTT treatment (FIGS. 11D&E). In a reducing environment, however, the size distribution peaks for the siRNA/poly(CBA-DAH-R) polyplexes at 200 nm particle size disappeared and the zeta potential was almost neutral (−2.7±0.4 mV) (FIGS. 11B&C), suggesting the polyplexes were completely degraded due to the reductive cleavage of the multiple disulfide linkages in the poly(CBA-DAH-R).

Example 10

Electrophoretic Mobility Shift Assay of siRNA/poly(CBA-DAH-R) Complexes

Figure 12A:
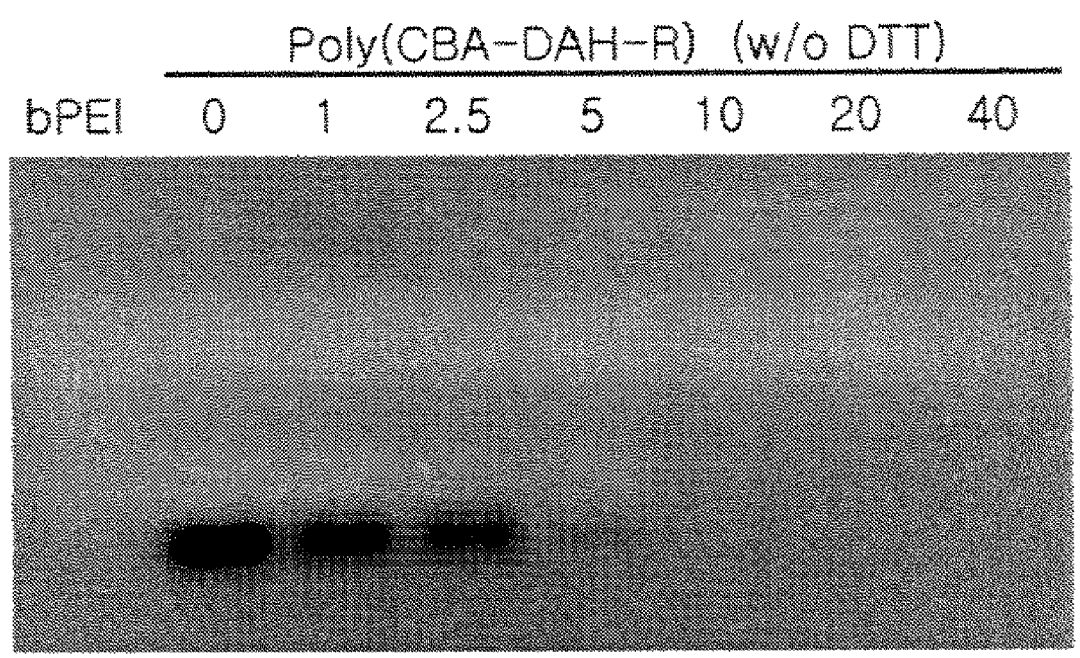
FIGS. 12A&B show gel retardation assays of siRNA/poly (CBA-DAH-R) polyplexes at various weight ratios without DTT treatment (FIG. 12A) and with 2.5 mM DTT (FIG. 12B). Control siRNA/bPEI polyplexes ("bPEI") were formulated at a weight ratio of 1:1.
Figure 12B:
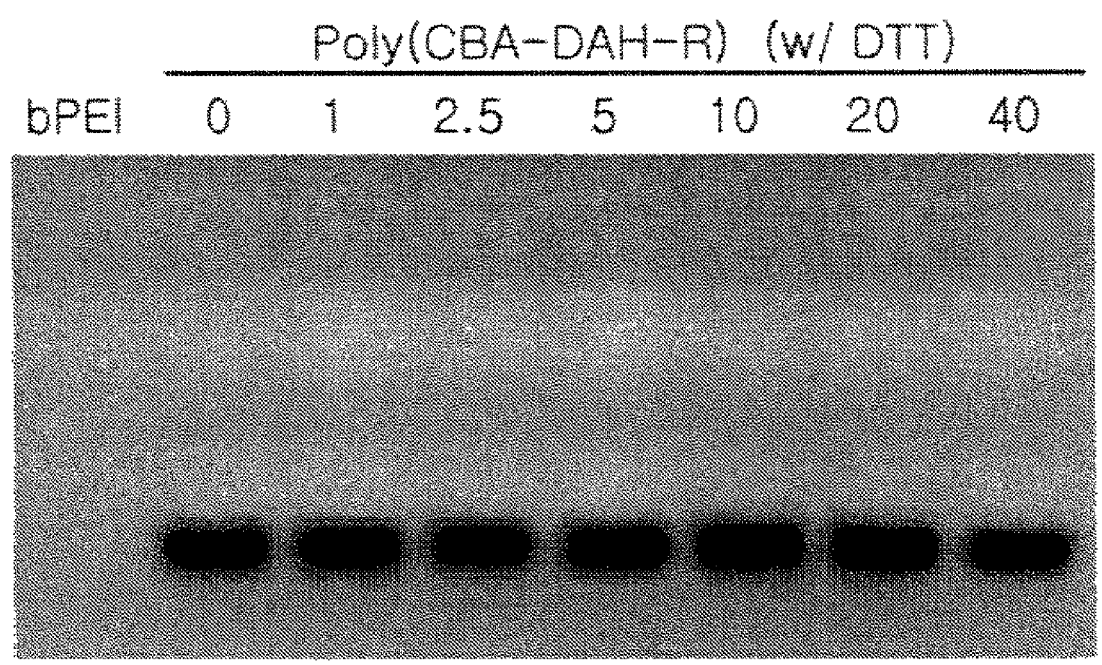

The unique structural characteristics of poly(CBA-DAH-R) were further confirmed in electrophoretic mobility shift assays (FIGS. 12A&B). Polyplexes of siRNA/poly(CBA-DAH-R) were prepared at different weight ratios (polymer/siRNA) ranging from 0:1 to 40:1. The siRNA (0.3 μg) was condensed with varying amounts of poly(CBA-DAH-R) in an aqueous phase (30 μL PBS, pH 7.4) and incubated at room temperature for 30 min. The siRNA/bPEI polyplexes were formed at a weight ratio of 1:1. Each sample solution was loaded onto a 2.0% agarose gel. Electrophoresis was carried out with a current of 120 V for 15 min in 1×TAE buffer solution (10 mM Tris/HC1, 1% (v/v) acetic acid, 1 mM EDTA). The retardation of the polyplexes was visualized with an image analyzer equipped with a UV transilluminator (GelDoc, BioRad, Hercules, Calif.) after ethidium bromide staining. To characterize the cleavability of poly(CBA-DAH-R) under reducing conditions, the polyplexes were preincubated with 2.5 mM DTT for 2 h at 37° C. prior to electrophoresis.

Poly(CBA-DAH-R) fully condensed siRNA molecules at weight ratios above 20:1, correlating with the particle formation data determined by DLS analysis (FIGS. 11A-E). A reducing environment caused complete siRNA release from the siRNA/poly(CBA-DAH-R) polyplexes as a result of degradation of the polymers, while the structure of the siRNA/bPEI polyplexes was not affected by a reducing environment. Previous studies have shown that polydisulfide polycations exhibit efficient unpackaging of the polyplexes by the cleavage of disulfide bonds in reductive conditions, which is responsible for the release of nucleic acids. M. Ou, X. L. Wang, R. Xu, C. W. Chang, D. A. Bull & S. W. Kim, Novel biodegradable poly(disulfide amine)s for gene delivery with high efficiency and low cytotoxicity, 19 Bioconjugate Chem. 626-633 (2008); S. Futaki et al., Membrane permeability commonly shared among arginine-rich peptides, 16 J. Mol. Recognit. 260-264 (2003); J. S. Choi et al., Enhanced transfection efficiency of PAMAM dendrimer by surface modification with L-arginine, 99 J. Controlled Release 445-456 (2004). The triggered degradation behavior of the siRNA/poly(CBA-DAH-R) polyplexes increases RNA silencing efficiency by improving the localization of the siRNA to the cytoplasm.

Example 11

Cellular Toxicity Assay of siRNA/poly(CBA-DAH-R) Complexes

Figure 13:
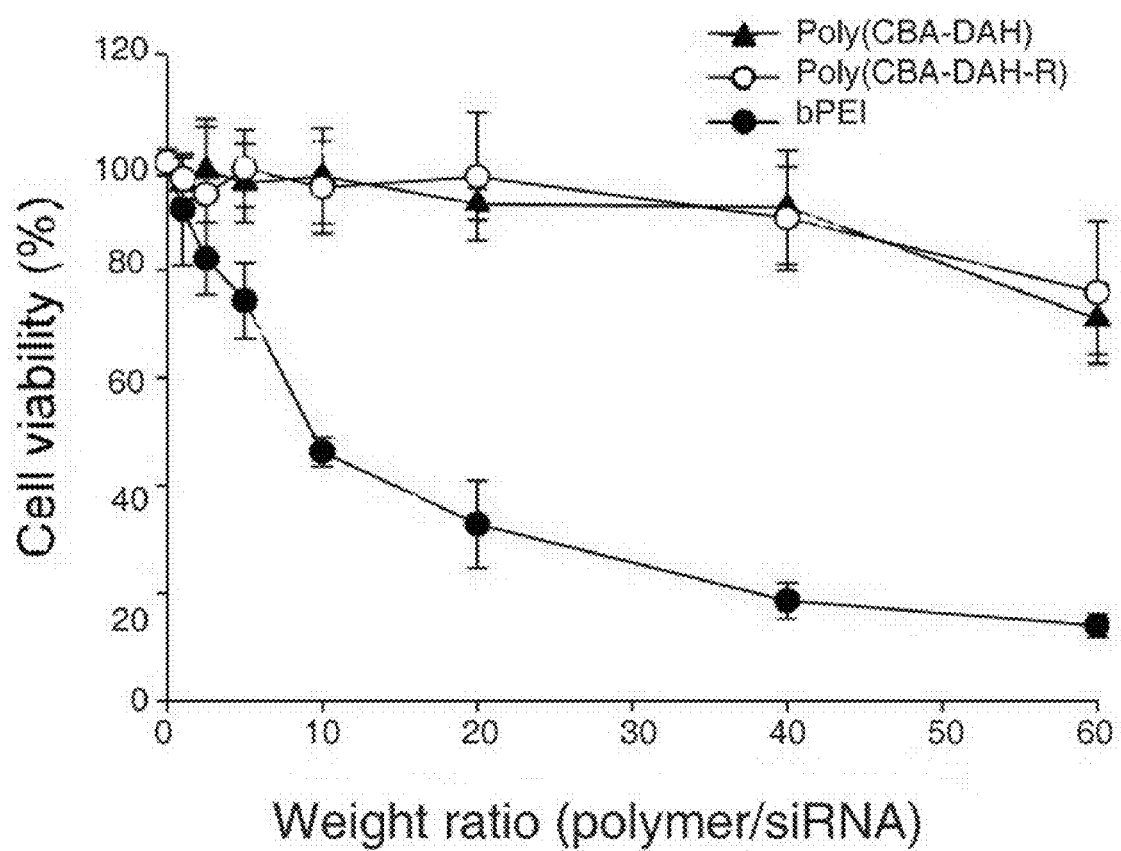
FIG. 13 shows cellular toxicity assay of poly(CBA-DAH) (▲), poly(CBA-DAH-R) (○), and bPEI (●) polyplexes with siRNA as a function of weight ratio (polymer/siRNA).

To assess the efficacy of poly(CBA-DAH-R) as an siRNA carrier in vitro, the cytotoxic activity of the siRNA/poly(CBA-DAH-R) polyplexes against PC-3 cells was evaluated by MTT assay (FIG. 13). Relative cell viability was determined using an MTT (Thiazolyl Blue Tetrazolium Bromide) assay. PC-3 cells were plated in 96-well plates at a density of $1\times10^4$ cells per well in 0.2 mL of culture medium and incubated for 24 h at 37° C. prior to polyplex treatment. The medium was replaced by a fresh serum-free transfection medium containing a desired amount of the siRNA polyplexes with poly(CBA-DAH), poly(CBA-DAH-R), and bPEI, which were formed at different weight ratios (polyer/siRNA) from 0:1 to 60:1. The polyplexes were prepared using 0.15 μg of siRNA and varying amounts of the polymers in 0.1 mL of PBS (pH 7.4). Cells were transfected by the polyplexes for 4 h at 37° C. and further incubated in a fresh serum-containing medium for 24 h at 37° C. Fifty microliters of MTT solution (2 mg/mL) were added and incubated at 37° C. for 4 h. The produced formazan crystals were dissolved in 0.2 mL of DMSO followed by plate reading at 530 nm in a microplate reader (Bio-Rad 680, Hercules, Calif.). The cell viability was determined relative to the untreated control cells.

The siRNA/poly(CBA-DAH-R) polyplexes had much lower cytotoxicity than the bPEI formulations. Poly(CBA-DAH-R) exhibited nearly 100% relative cell viability at weight ratios up to 40:1, while bPEI showed only 40% relative cell viability at a weight ratio near 10:1. There was no meaningful difference in cellular toxicity between the unmodified and the arginine-modified reducible polymers, suggesting that the arginine modification does not affect the biocompatibility of bioreducible cationic polymers. The cytotoxicity of polycations is caused by an increase in molecular weight as well as cationic charge density. D. Fischer et al., In vitro cytotoxicity testing of polycations: influence of polymer structure on cell viability and hemolysis, 24 Biomaterials 1121-1131 (2003). The cytotoxicity of higher molecular weight polycations, however, decreases with breakdown into lower molecular weight components. Y. H. Park, J. H. Park, M. Lee, Y. H. Kim, T. G. Park & S. W. Kim, Polyethylenimine with acid-labile linkages as a biodegradable gene carrier, 103 J. Controlled Release 209-219 (2005). Thus, the improved cell viability of poly(CBA-DAH-R) may be attributable to its biodegradability. Further in vitro studies conducted at nontoxic levels of bPEI, poly(CBA-DAH), and poly(CBA-DAH-R) formulations displayed over 90% cell viability with weight ratios under 1:1, 40:1, and 40:1, respectively.

Example 12

Flow Cytometry of siRNA/poly(CBA-DAH-R) Polyplexes

To investigate the influence of the arginine modification of poly(CBA-DAH-R) on transfection efficiency, the cellular uptake of fluorescently labeled siRNA formulations by PC-3 cells was monitored using flow cytometric analysis. The siRNA polyplexes with poly(CBA-DAH), poly(CBA-DAH-R), and bPEI were used at weight ratios (polymer/siRNA) of 40:1, 40:1, and 1:1, respectively. At the chosen weight ratios of polymer to siRNA, the corresponding calculated charge ratios for poly(CBA-DAH), poly(CBA-DAH-R), and bPEI were 43:1, 25:1, and 8:1, respectively. PC-3 cells were plated in 6-well plates at an initial density of $2.5\times10^5$ cells per well for flow cytometry analysis. The siRNA polyplexes were formed with 0.75 μg of Cy3-siRNA and a selected amount of the polymers in an aqueous buffer solution (0.1 mL PBS, pH 7.4) for 15 min at room temperature. The Cy3-siRNA formulations, including naked siRNA, siRNA/poly(CBA-DAH), siRNA/poly(CBA-DAH-R), and siRNA/bPEI polyplexes, were added to the wells containing a serum-free transfection medium. Prior studies had demonstrated that the transfection efficiencies for the Cy3-siRNA formulations did not differ between 4, 8, 12, and 24 h of incubation, so incubation times of 4 h for the Cy3-siRNA formulations were used throughout the experiments. After 4 h of incubation, cells were washed four times with cold PBS, harvested by trypsin digestion, and fixed in 75% ethanol solution for 30 min at 4° C. Cells were analyzed on a flow cytometer (FACS Caliber, Becton-Dickinson, Mountain View, Calif.) using FL2 channel (Ex. 488 nm/Em. 575 nm). Data were processed using Windows Multiple Document interface software (WinMDI).

Figure 14:
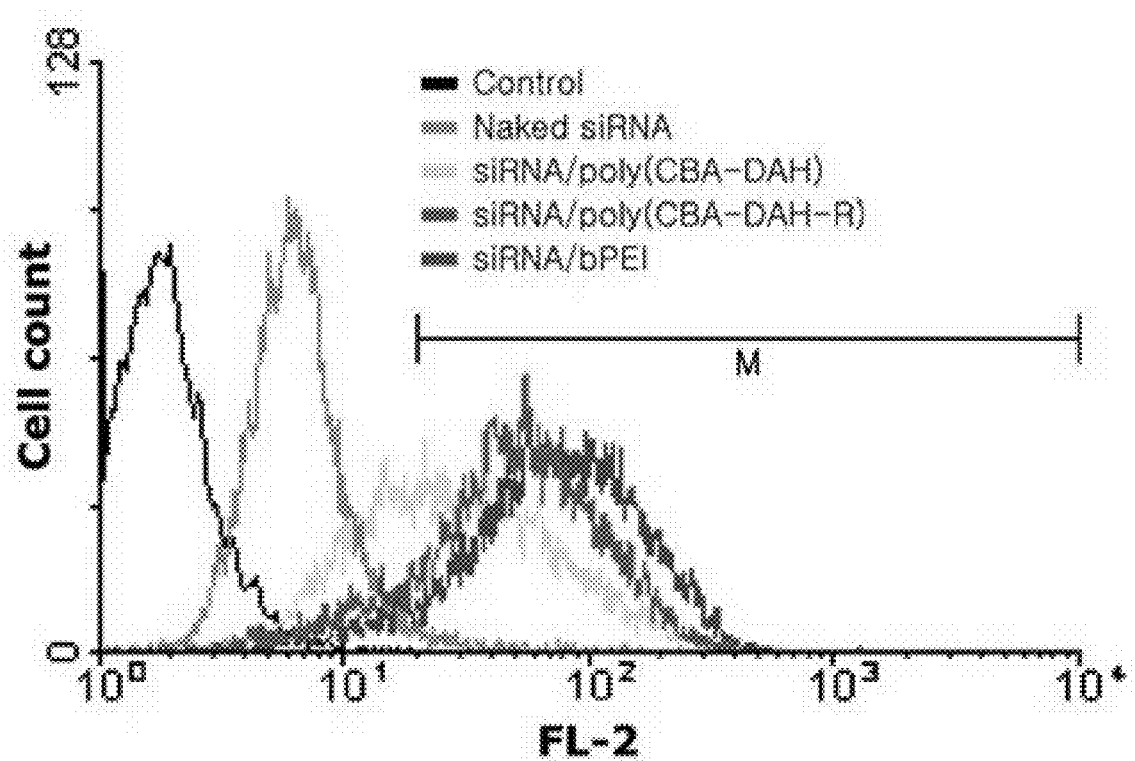
FIG. 14 shows representative flow cytometric histograms of PC-3 cells transfected with naked siRNA (ref. no. 100), siRNA/poly(CBA-DAH) (ref. no. 102), siRNA/poly(CBA-DAH-R) (ref. no. 104), and siRNA/bPEI (ref. no. 106). Control cells (ref. no. 108) are also shown. Cy3-modified siRNA was used. M presents a gated region (fluorescence intensity (arbitrary unit): 350-10,000).
Figure 15A:
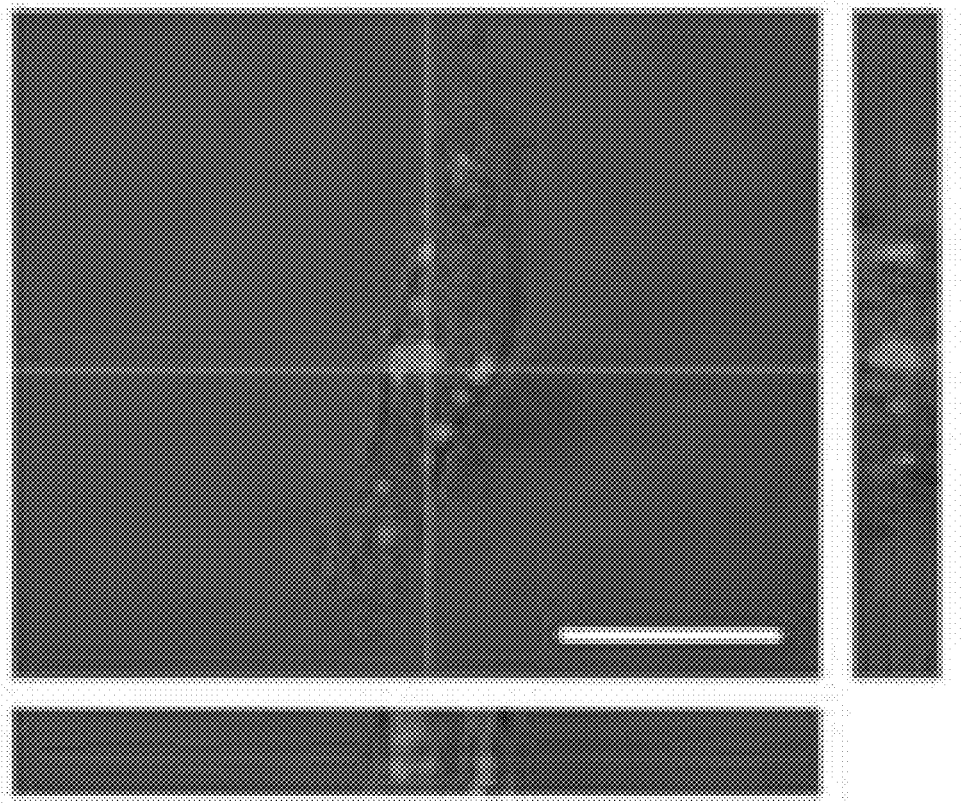
FIGS. 15A-H show subcellular confocal images of cytoplasmic siRNA release of siRNA/poly(CBA-DAH-R) (FIGS. 15B, 15D, 15F, 15H) and siRNA/bPEI (FIGS. 15A, 15C, 15E, 15G) polyplexes with (FIGS. 15C, 15D, 15G, 15H) and without (FIGS. 15A, 15B, 15E, 15F) the glutathione-depleting agent, BSO. Cy3-modified siRNA was used. Scale bars represent 10 μm.
Figure 15B:
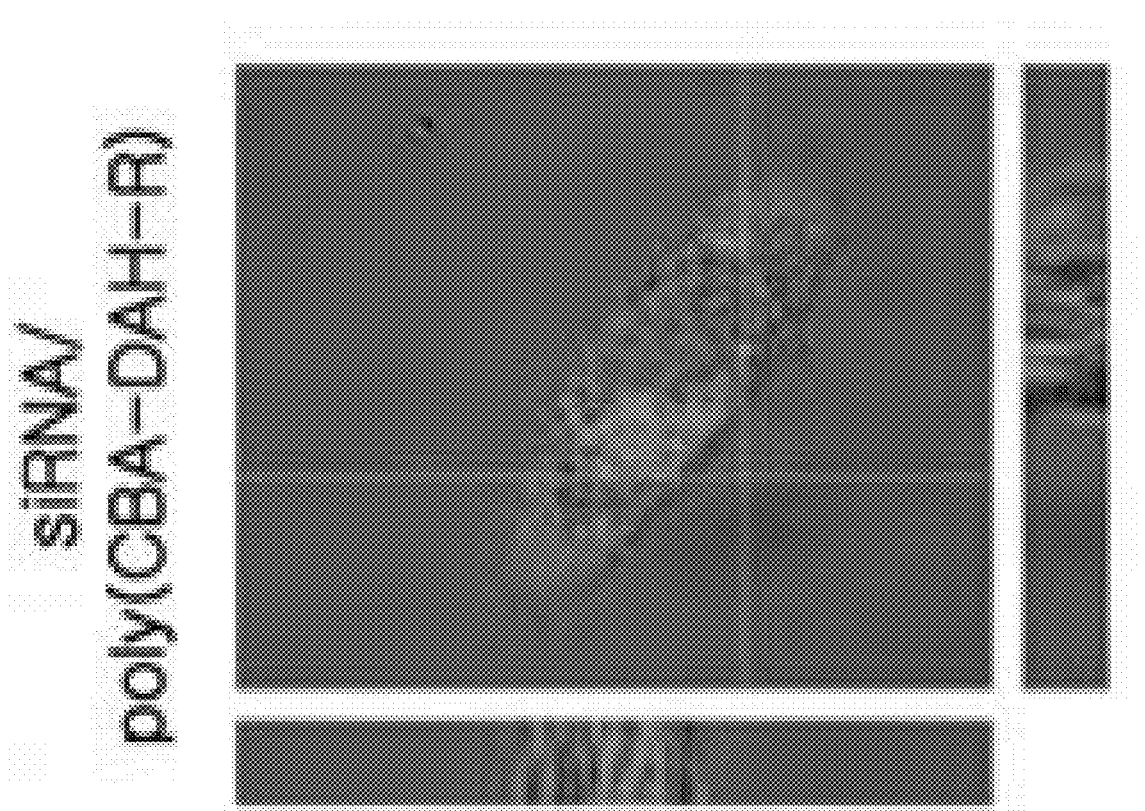
Figure 15C:
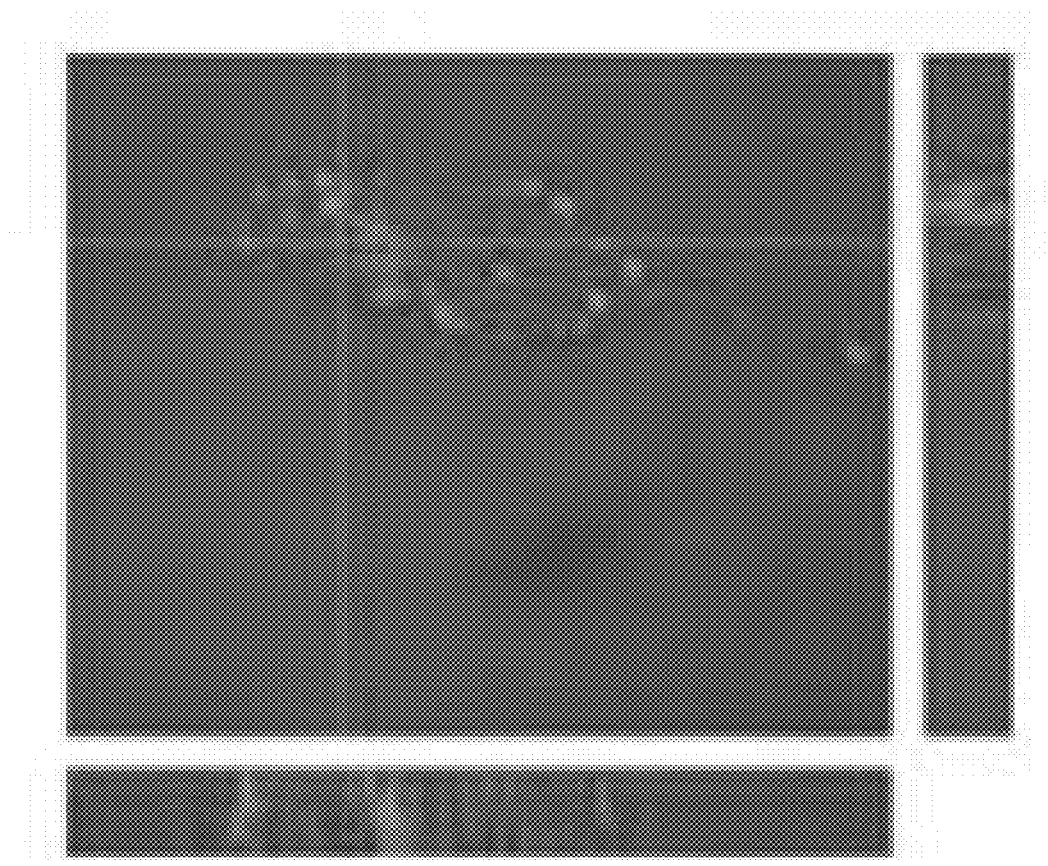
Figure 15D:
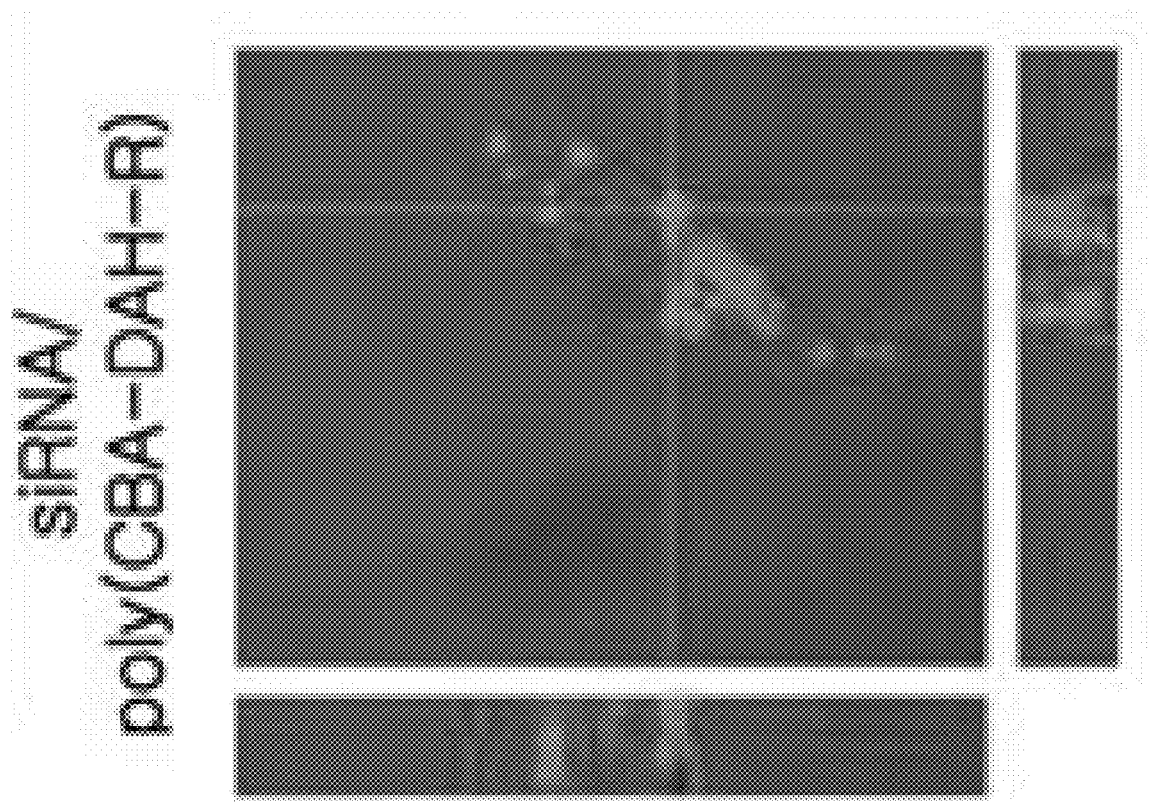
Figure 15E:
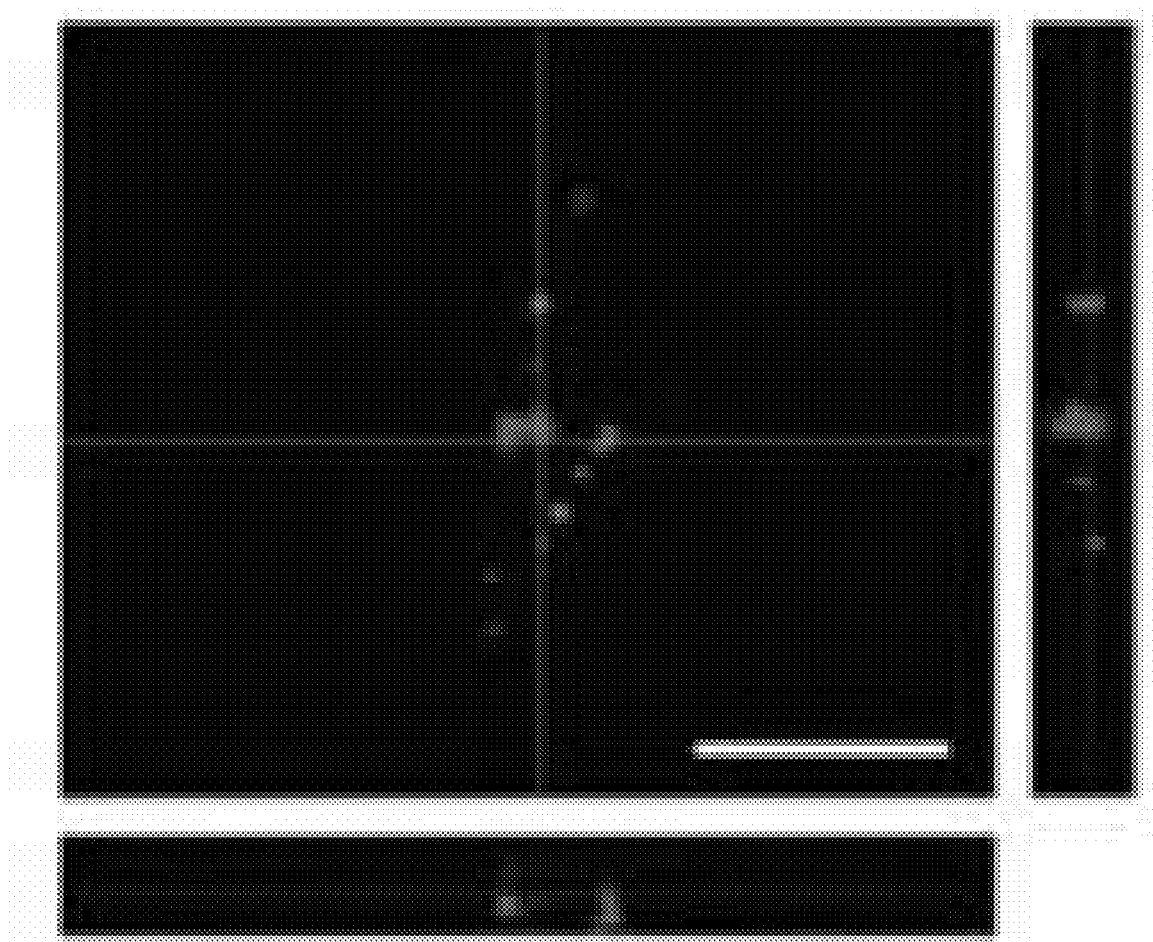
Figure 15F:
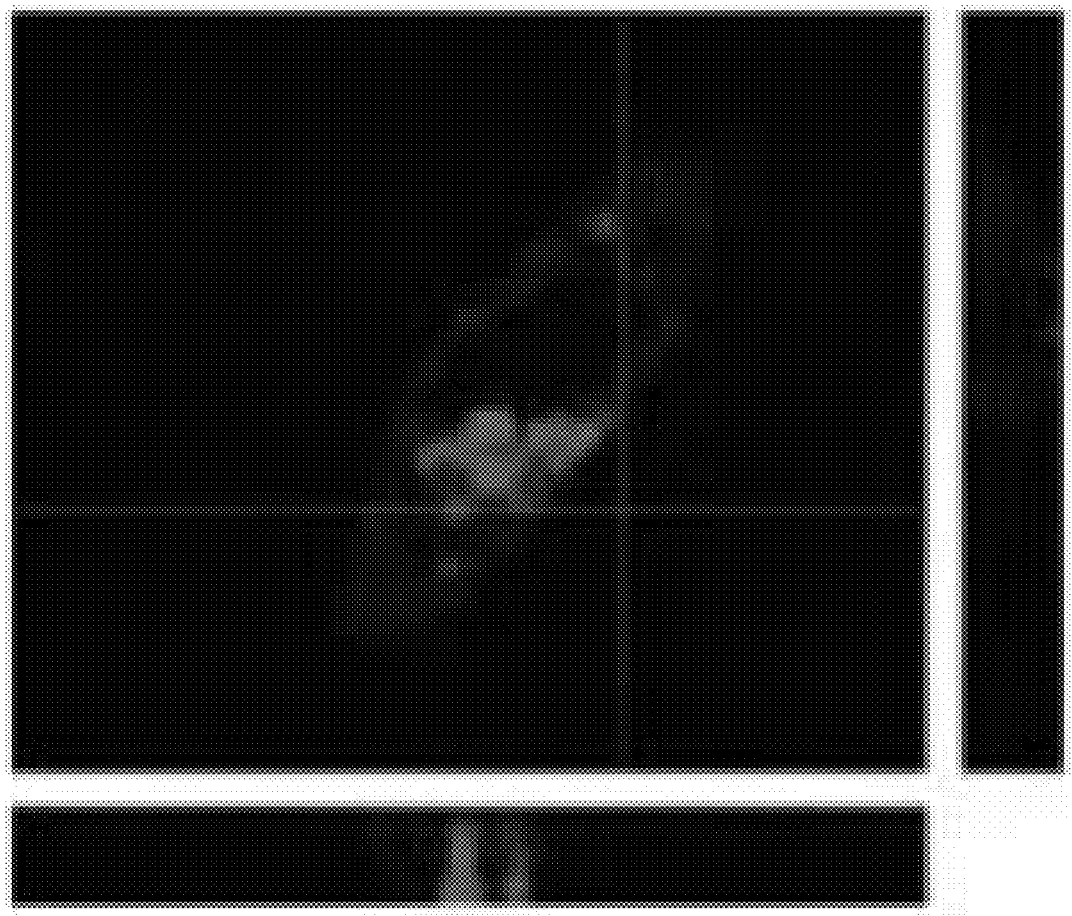
Figure 15G:
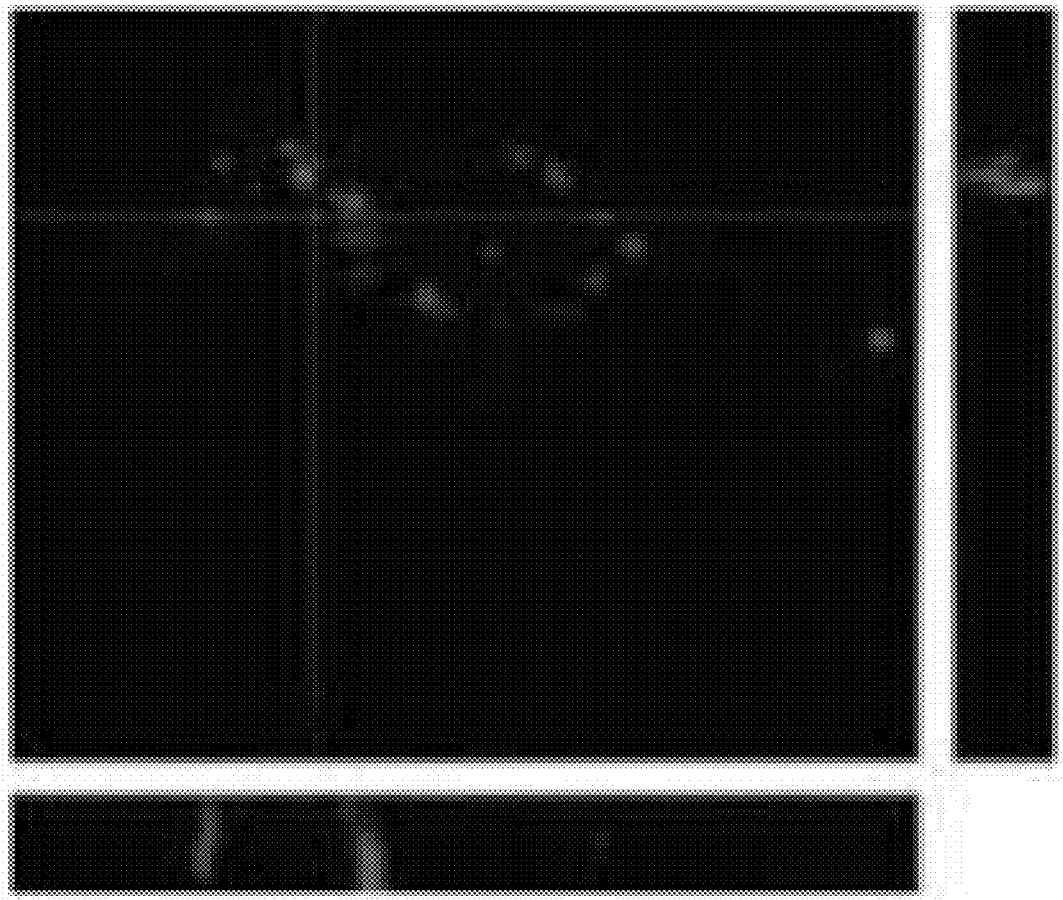
Figure 15H:
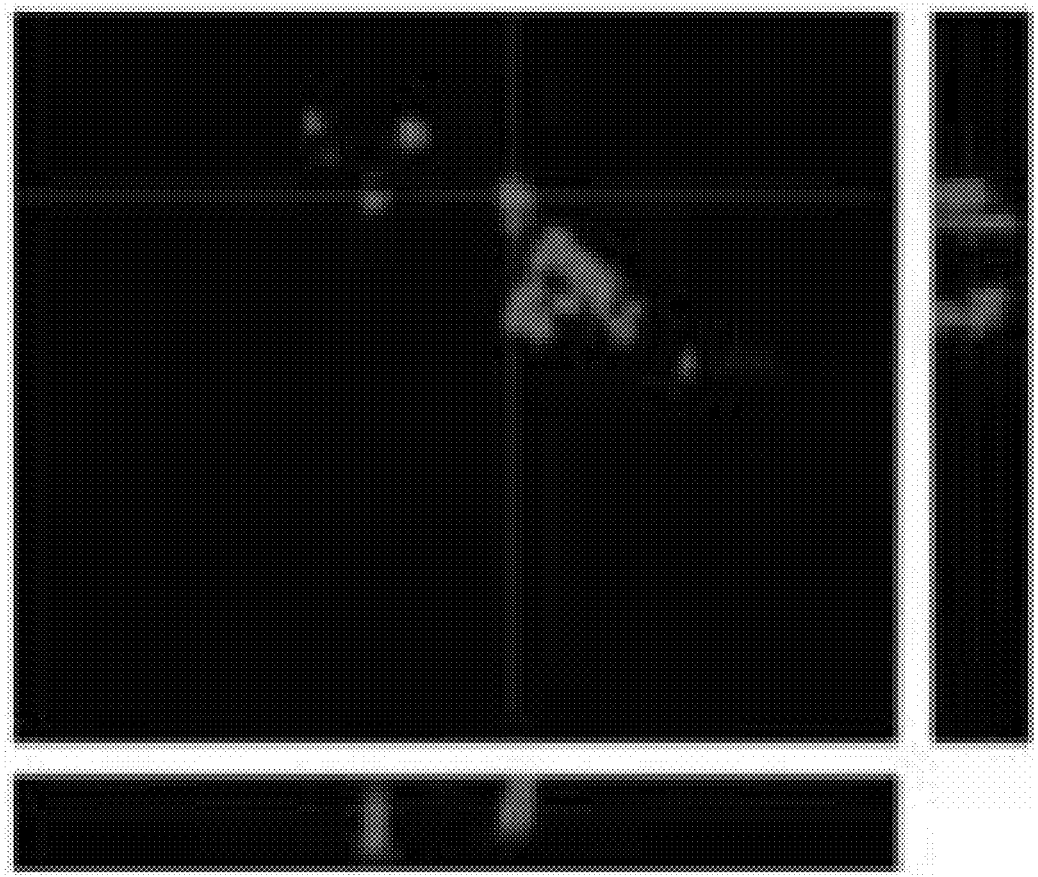

As shown in FIG. 14, most of the control (ref. no. 108) and the naked siRNA (ref. no. 100) treatment groups showed very low fluorescence intensity. However, the fluorescence peaks for the cells treated with various polyplex formulations were notably shifted to the right. The percentage of the cells gated from region M for the siRNA/poly(CBA-DAH) (ref. no. 102), siRNA/poly(CBA-DAH-R) (ref. no. 104), and siRNA/bPEI polyplexes (ref. no. 106) was 57.0%, 81.0%, and 88.2%, respectively. The extent of cellular uptake of the siRNA/poly (CBA-DAH-R)(104) polyplexes was 1.4-fold greater than that of the siRNA/poly(CBA-DAH) (102) polyplexes. There was no significant difference, however, between poly(CBA-DAH-R) (104) and bPEI (106) in the cellular uptake of the polyplexes. The enhanced delivery of the siRNA/poly(CBA-DAH-R) (104) polyplexes is likely due to the arginine modification of the polydisulfide cationic polymers. Arginine residues, which are rich in membrane translocalization peptides, help enhance the cellular association and membrane permeability of many biologically active products. W. J. Kim, L. V. Christensen, S. Jo, J. W. Yockman, J. H. Jeong, Y. H. Kim & S. W. Kim, Cholesteryl oligoarginine delivering vascular endothelial growth factor siRNA effectively inhibits tumor growth in colon adenocarcinoma, 14 Mol. Ther. 343-350 (2006).

Example 13

Confocal Microscopy of siRNA/poly(CBA-DAH-R) Polyplexes

To verify that reductive degradation of siRNA/poly(CBA-DAH-R) polyplexes leads to improved RNA silencing, confocal microscopic observations on subcellular localization of fluorescein binding siRNA were carried out using PC-3 cells. PC-3 cells were seeded in confocal imaging dishes (Glass Bottom microwells, MatTek Corp., Ashland, Mass.) at a density of $1 \times 10^4$ cells per well. Cells were preincubated for 24 h prior to transfection in the presence or absence of 10 mM DL-buthionine-sulfoxamine (BSO), which causes a significant decrease in the intracellular level of reduced glutathione (GSH). The siRNA polyplexes, which were prepared by the same method described above, were transfected for 2 h at 37° C. The transfection medium was replaced with a fresh culture medium and the cells were incubated for a further 3 h at 37° C. The cells were washed with cold PBS four times and fixed with 0.5% para-formaldehyde solution for 30 min at 4° C. The localization of Cy3-labeled siRNA within the cells was visualized with a confocal laser scanning microscope (Olympus Fluoview FV300, Melville, N.Y.) with a 100× oil-immersion objective lens using an argon/krypton mixed gas laser (Ex. 568 nm). Three-dimensional confocal images for the cells were constructed using Velocity software (Improvision Inc., Lexington, Mass.).

FIGS. 15A-H show that in cells transfected by the siRNA/poly(CBA-DAH-R) polyplexes, siRNA was evenly distributed throughout the cytoplasm. However, the cytoplasmic localization of siRNA was fully suppressed with the treatment of a glutathione depleting agent, BSO, which is known to inhibit intracellular reducing potential. S. Shalini & M. P. Bansal, Co-operative effect of glutathione depletion and selenium induced oxidative stress on API and NfkB expression in testicular cells in vitro: insights to regulation of spermatogenesis, 40 Biol. Res. 307-317 (2007). These findings demonstrate that intact siRNA molecules were successfully released from the destabilized polyplexes due to the degradation of the polymer backbones in the reductive environment of the cytoplasm. In contrast, small fluorescent spots were observed throughout the cells when transfected with the siRNA/bPEI polyplexes, irrespective of the presence or absence of BSO, suggesting that most of the siRNA molecules were still complexed in the large bPEI polyplex aggregates due to the limited degradation of the bPEI polyplexes and release of siRNA at the cellular level. These observations indicate that the triggered release of siRNA from the siRNA/poly(CBA-DAH-R) polyplexes could play a critical role in enhancing RNA silencing.

Example 14

In Vitro Transfection with siRNA/poly(CBA-DAH-R) Complexes

To assess the potential efficacy of siRNA therapy for cancer, the RNAi activity of the siRNA/poly(CBA-DAH-R) polyplexes was evaluated in human prostate carcinoma PC-3 cells using siRNA targeted against VEGF. For in vitro transfection studies, $2.5 \times 10^5$ cells (PC-3, KB, HeLa, A2780, and A549) per well were plated in a 6-well plate. After 24 h of incubation, the culture medium was replaced prior to transfection by the transfection medium with or without 10% FBS. To decrease the intracellular reduction potential, cells were preincubated for 24 h prior to transfection in the presence or absence of 10 mM BSO at 37° C. VEGF siRNA (1.5 µg) was condensed with a selected amount of the polymers in 0.2 mL of PBS. The VEGF siRNA polyplexes were left at an ambient temperature for 30 min and added into the transfection medium. After 4 h of transfection at 37° C., the transfection medium was replaced with a fresh medium containing 10% FBS and continuously incubated for a further 8 h. The medium was then removed and supplemented with fresh culture medium containing heparin (20 µg/mL). After 18 h of incubation, the medium was collected for VEGF ELISA assay. The amount of VEGF secreted from the cells was determined using a human VEGF immunoassay kit (R&D Systems, Minneapolis, Minn.) according to the manufacturer's instructions. All of the data are presented as the mean±standard deviation (SD) of three independent measurements. Statistical analysis was carried out by a Student's t test. Statistical significance was assigned for p values<0.05.

Figure 16:
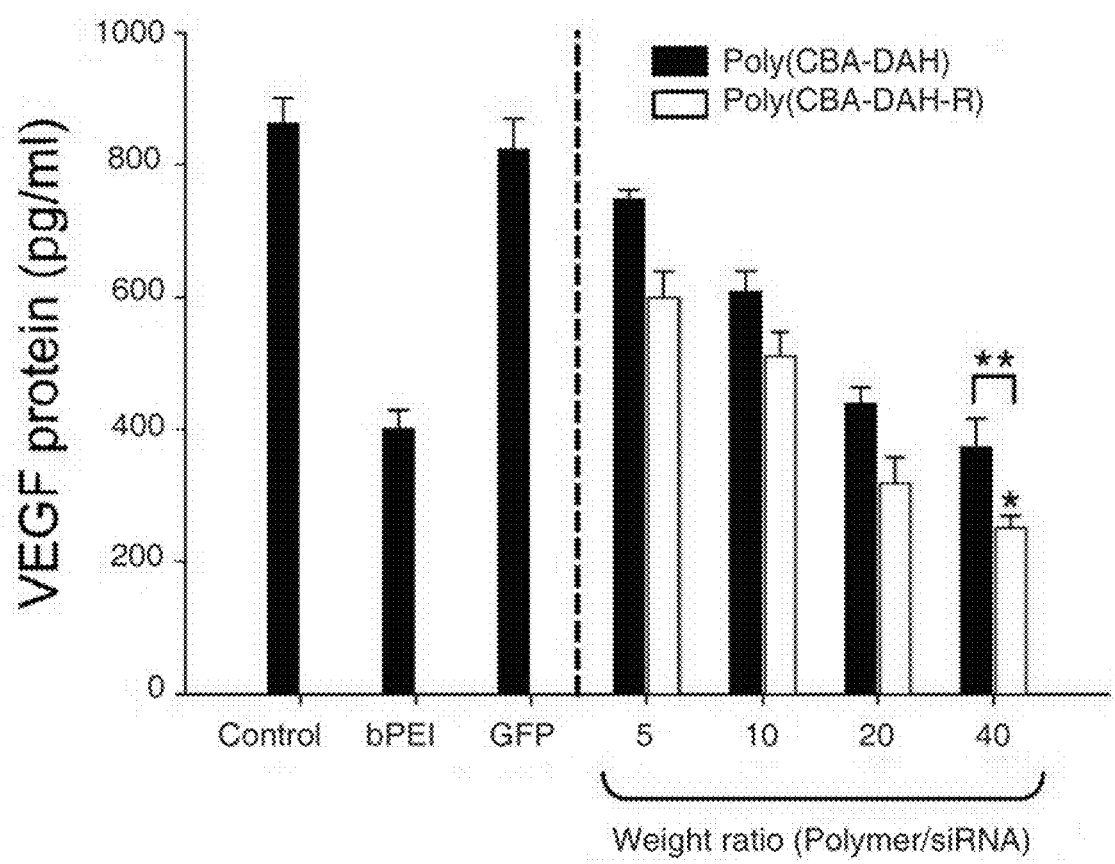
FIG. 16 shows VEGF gene silencing of VEGF siRNA/poly (CBA-DAH-R) polyplexes at various weight ratios (polymer/siRNA). PC-3 cells were transfected with bPEI (weight ratio 1:1), poly(CBA-DAH), and poly(CBA-DAH-R) formulations with VEGF siRNA. GFP siRNA/bPEI polyplexes were controls. Statistical significance, * =p<0.05 versus bPEI, **=p<0.05 versus poly(CBA-DAH). The VEGF expression was analyzed using ELISA for human VEGF.

VEGF has a predominant role in tumor angiogenesis. S. H. Kim, J. H. Jeong, S. H. Lee, S. W. Kim & T. G. Park, Local and systemic delivery of VEGF siRNA using polyelectrolyte complex micelles for effective treatment of cancer, 129 J. Controlled Release 107-116 (2008); D. J. Hicklin & L. M. Ellis, Role of the vascular endothelial growth factor pathway in tumor growth and angiogenesis, 23 J. Clin. Oncol. 1011-1027 (2005). The VEGF siRNA polyplex formulations silenced VEGF gene expression in a sequence specific manner (FIG. 16). Both the siRNA polyplexes with poly(CBA-DAH) and poly(CBA-DAH-R) decreased VEGF expression. As expected, the arginine-containing polyplexes showed consistently greater gene silencing efficiency than the unmodified polyplexes, presumably resulting from the enhanced cellular uptake of the siRNA/poly(CBA-DAH-R) polyplexes. The VEGF siRNA/poly(CBA-DAH-R) polyplexes formulated at a weight ratio of 40:1 exhibited prominent VEGF silencing activity, compared to the VEGF siRNA/poly(CBA-DAH) and VEGF siRNA/bPEI (a weight ratio of 1:1) polyplexes. Meanwhile, the VEGF siRNA/poly(CBA-DAH) polyplexes demonstrated a similar level of VEGF silencing as the bPEI formulations, though the siRNA/poly(CBA-DAH) polyplexes showed a lower level of cellular association than the siRNA/bPEI polyplexes (FIG. 14). These results imply that high-efficiency uptake of siRNA polyplexes does not necessarily guarantee the RNAi activity of siRNA therapeutics. In addition to enhancing the cellular delivery with arginine modification, the unique structural characteristic of poly(CBA-DAH-R) appears to exert considerably more influence in siRNA-mediated gene silencing compared to other polymer carriers.

Figure 17:
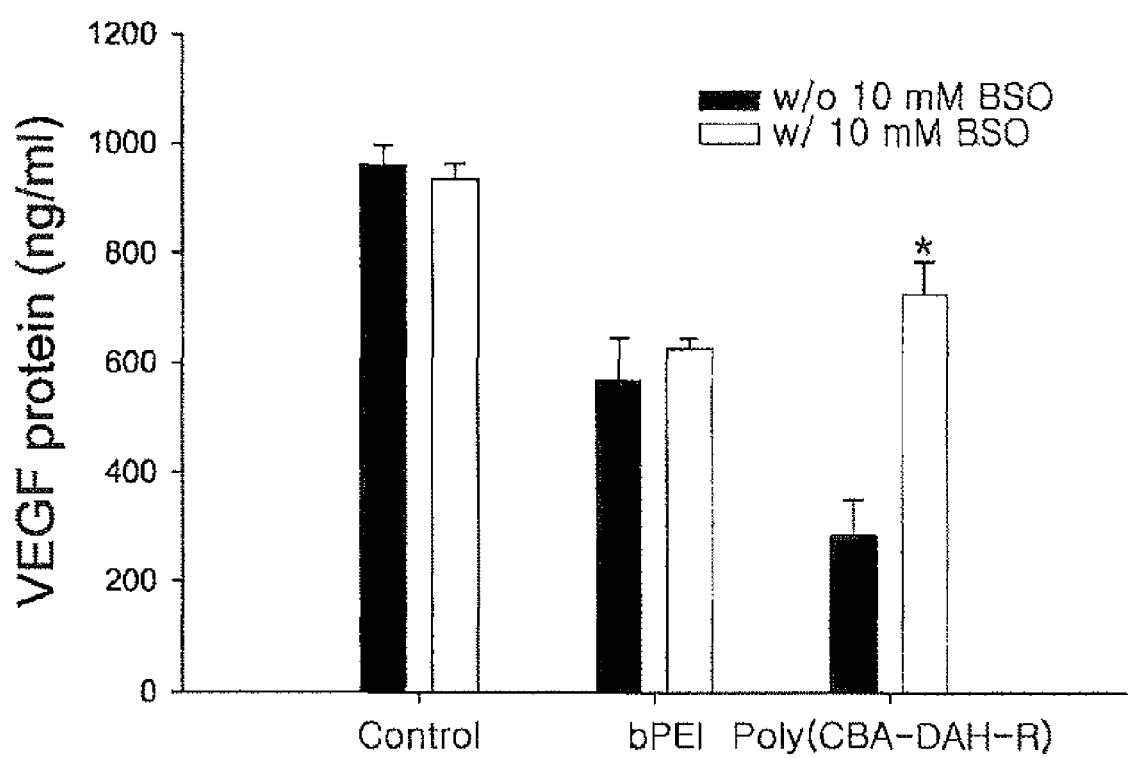
FIG. 17 shows the effect of the glutathione-depleting agent, BSO, on VEGF gene silencing of VEGF siRNA/poly (CBA-DAH-R) polyplexes in PC-3 cells. Cells were pretreated with (open bars) or without (dark bars) 10 mM BSO for 24 h prior to transfection. Statistical significance, *=p<0.01 versus without 10 mM BSO.

To further confirm the interpretation that triggered release of siRNA from siRNA/poly(CBA-DAH-R) polyplexes play a critical role in enhancing RNA silencing, VEGF gene silencing experiments in PC-3 cells were conducted under both reducing and nonreducing conditions (FIG. 17). When the VEGF siRNA/poly(CBA-DAH-R) polyplexes were transfected in the presence of 10 mM BSO, VEGF expression was significantly higher, while the bPEI polyplexes exhibited the same level of RNAi activity against VEGF expression in both BSO treated and BSO untreated cells. These results indicate that the biodegradability of poly(CBA-DAH-R) increases the localization of siRNA to the cytoplasm.

Figure 18:
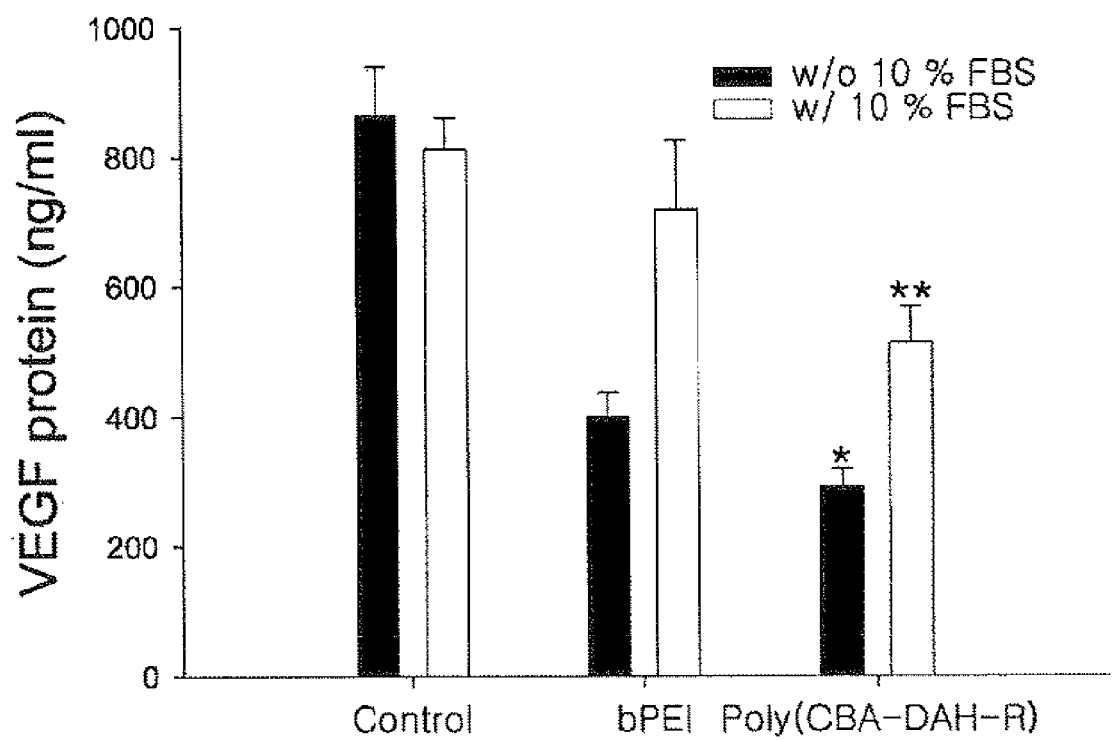
FIG. 18 shows the effect of serum proteins on VEGF gene silencing of VEGF siRNA/poly(CBA-DAH-R) polyplexes in PC-3 cells. Cells were transfected in media with (open bars) or without (dark bars) 10% FBS. Statistical significance, *=p<0.05 versus bPEI (without 10% FBS), **=p<0.01 versus bPEI (with 10% FBS). The amount of VEGF secreted from the cells was determined using ELISA for human VEGF.
Figure 19:
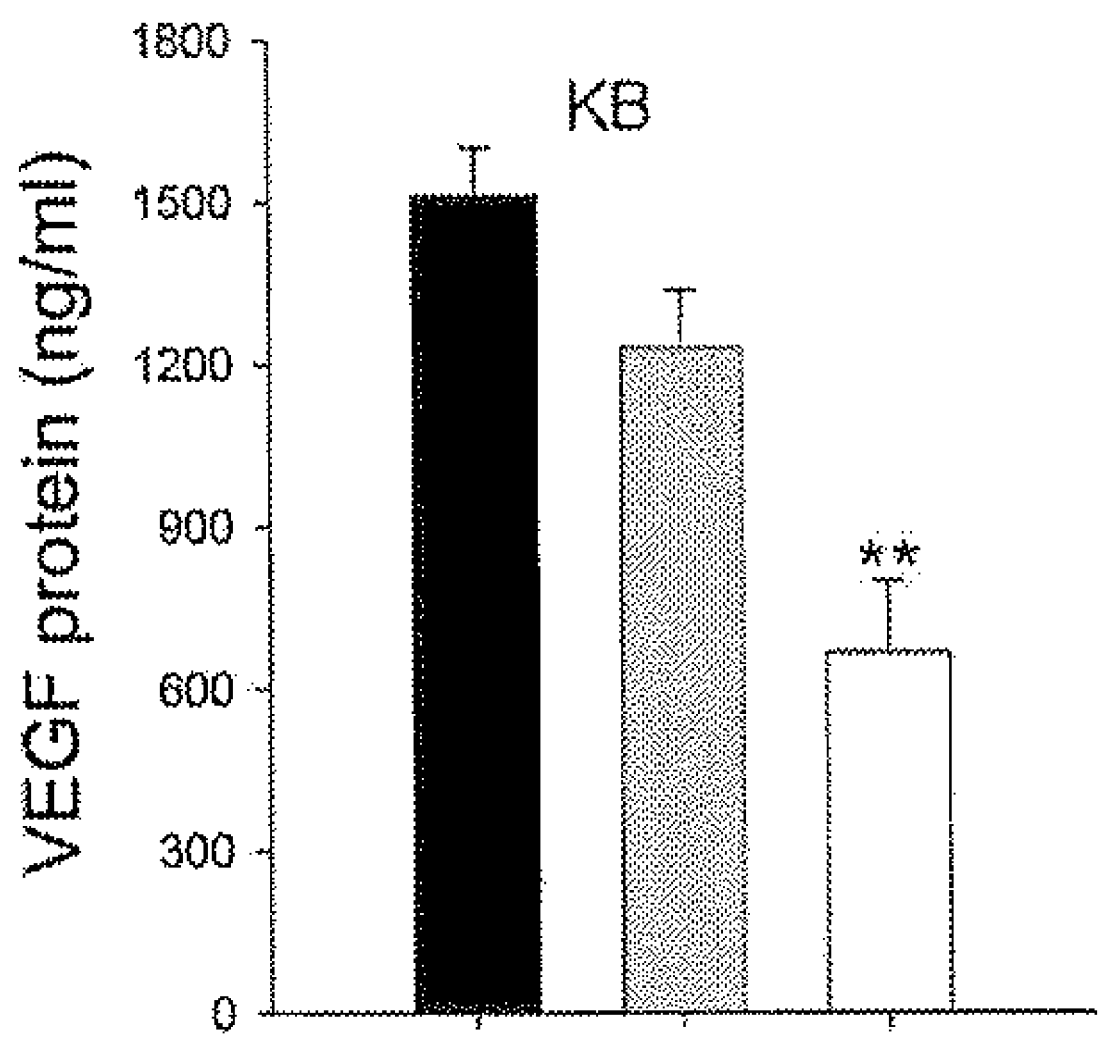
FIGS. 19-22 show VEGF gene silencing of VEGF siRNA/poly(CBA-DAH-R) polyplexes in various human cancer cells, KB, A2780, HeLa, and A549, respectively. Statistically significant differences from bPEI, *=p<0.05, **=p<0.01. The VEGF expression level was determined using ELISA for human VEGF.
Figure 20:
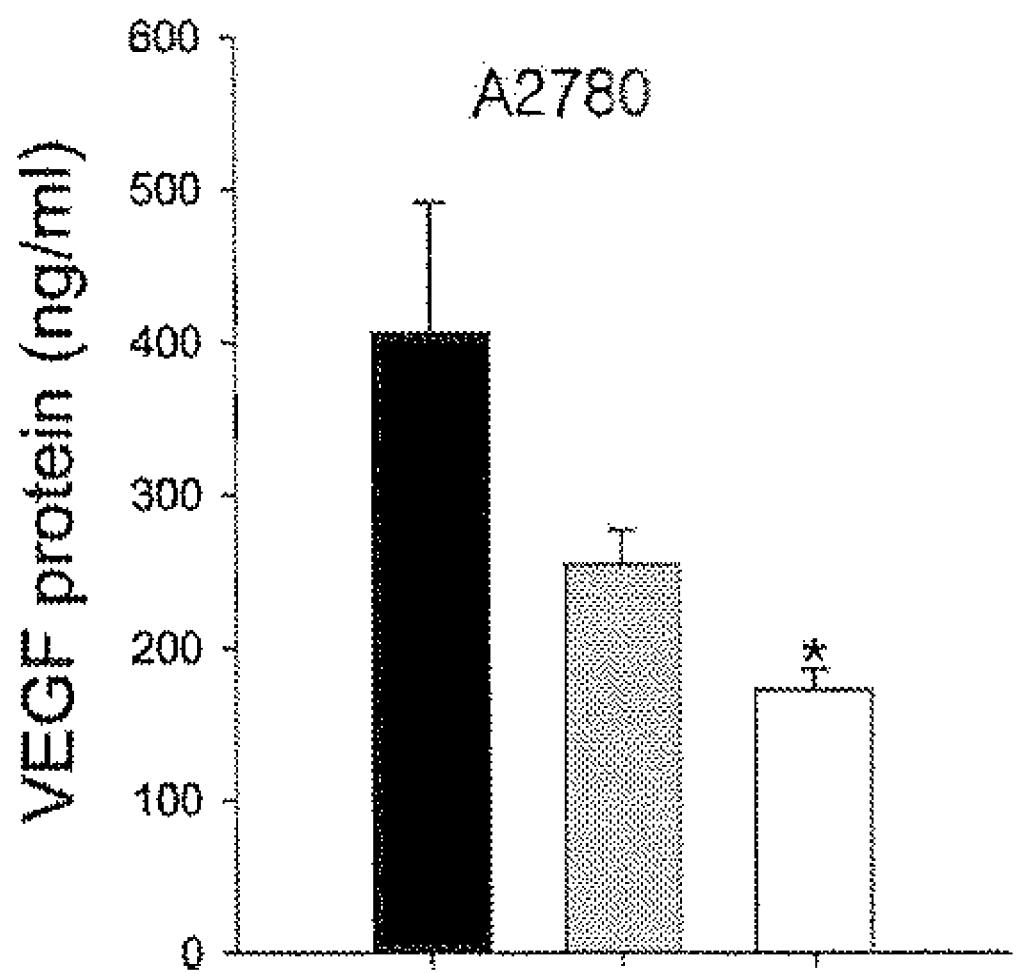
Figure 21:
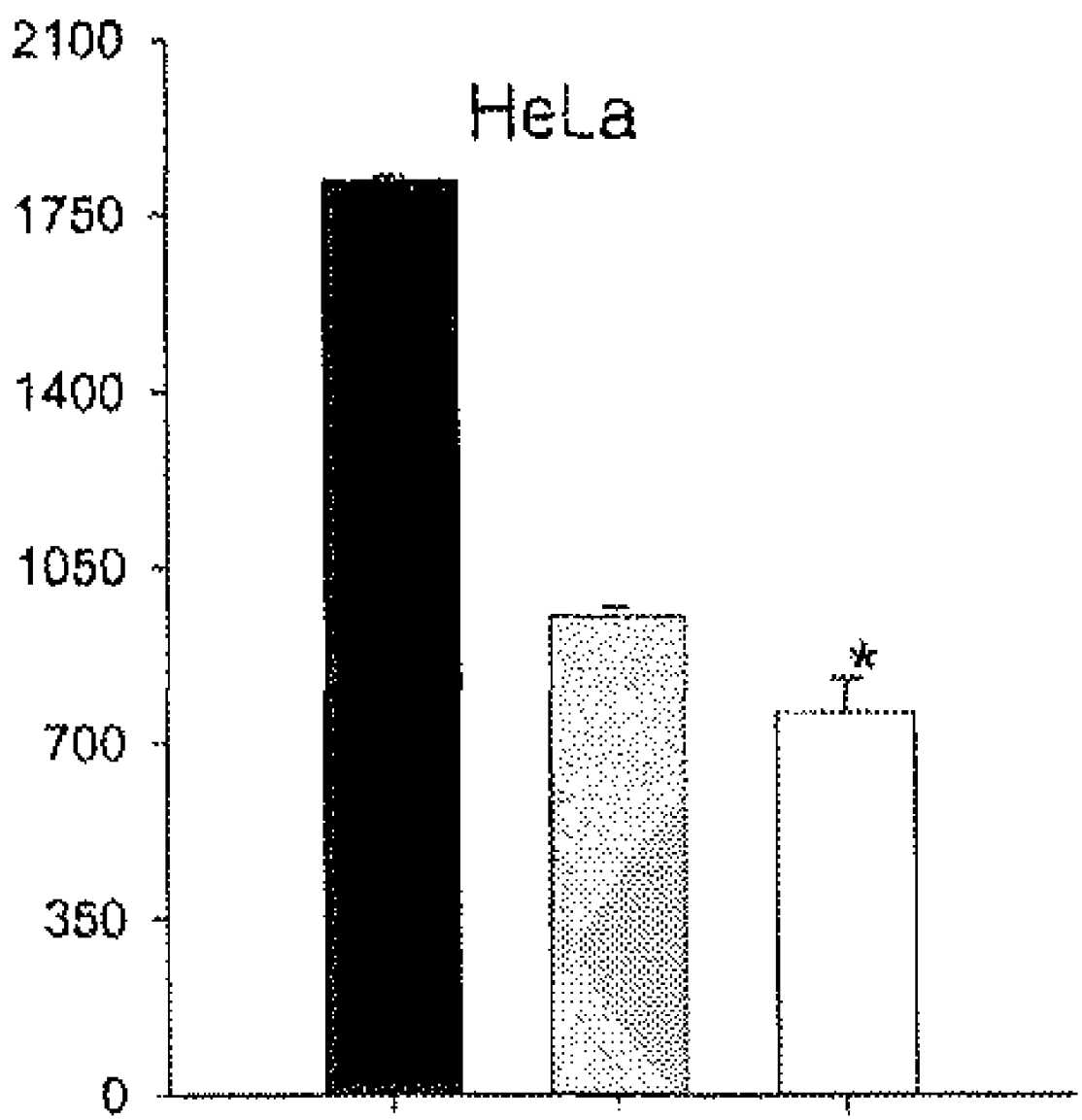
Figure 22:
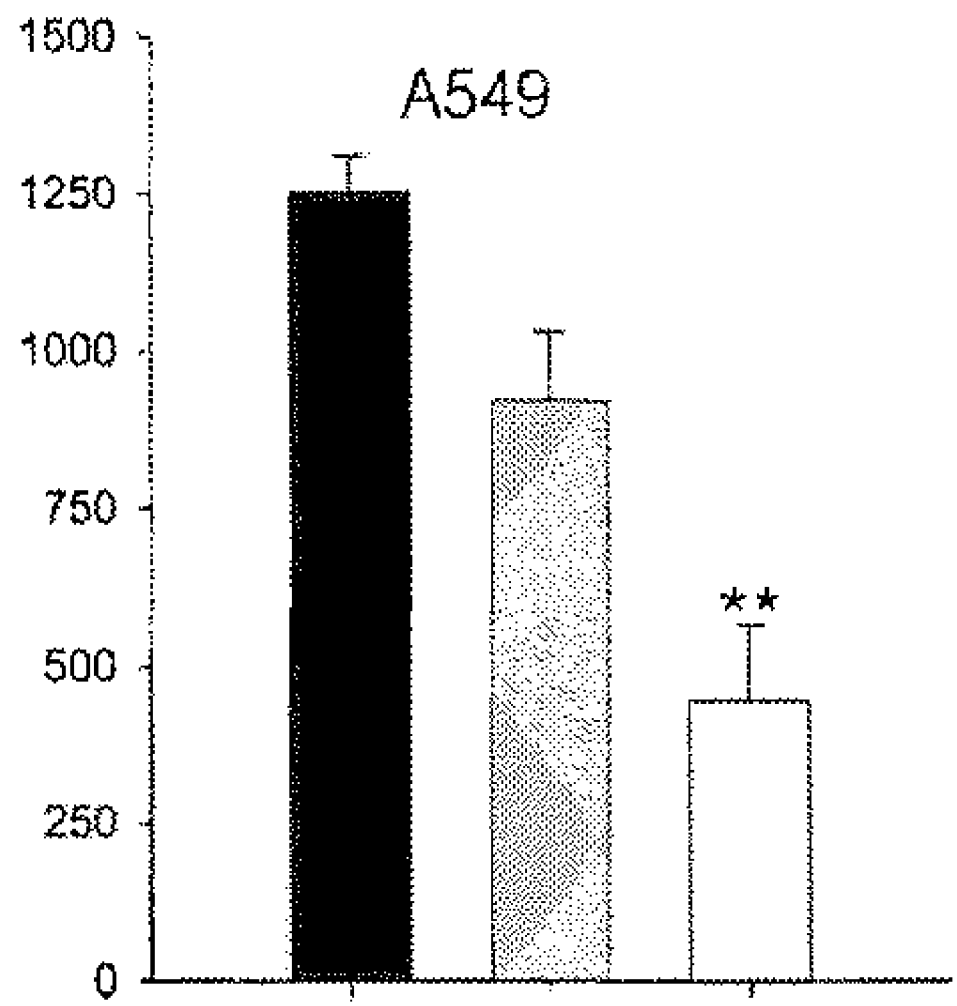

The influence of serum proteins on the VEGF gene silencing activity of VEGF siRNA/poly(CBA-DAH-R) polyplexes was evaluated by conducting transfection in the presence of 10% FBS (FIG. 18). Although both poly(CBA-DAH-R) and bPEI showed approximately a 2-fold reduction in RNAi activity in the presence of serum proteins, the VEGF siRNA/poly(CBA-DAH-R) polyplexes still exhibited a higher level of VEGF inhibition compared to the VEGF siRNA/bPEI polyplexes. These results suggest that the VEGF siRNA/poly(CBA-DAH-R) polyplex delivery system could be a potential approach for siRNA-based cancer therapy.

To assess the applicability of the VEGF siRNA/poly(CBA-DAH-R) formulation to a wide range of tumor types, the VEGF gene silencing activity of the VEGF siRNA/poly(CBA-DAH-R) polyplexes was further assessed in various human cancer cells including oral (KB), cervical (HeLa), ovarian (A2780), and lung (A549) in addition to the prostate carcinoma PC-3 cells (FIGS. 19-22). The cancer cell lines manifested different levels of VEGF production and VEGF inhibition by the VEGF siRNA formulations. It is known that cancer cells upregulate VEGF expression, but the degree of upregulation varies, depending on the cancer cell type. D. J. Hicklin & L. M. Ellis, supra; W. G. Roberts et al., Host microvasculature influence on tumor vascular morphology and endothelial gene expression, 153 Am. J. Pathol. 1239-1248 (1998). The differences in VEGF gene silencing of the VEGF siRNA/poly(CBA-DAH-R) polyplexes in varied cancer cell types are probably determined by differences in the levels of intracellular reducing potential, since different cells have different capacities for glutathione synthesis to maintain the reductive environment of the cytoplasm. W. Wang & N. Ballatori, Endogenous glutathione conjugates: occurrence and biological functions, 50 Pharmacol. Rev. 335-356 (1998). Poly(CBA-DAH-R) invariably exhibited higher RNAi activity than bPEI in all cancer cell lines tested, suggesting that the VEGF siRNA/poly(CBA-DAH-R) polyplex delivery system could be useful in the treatment of various types of human cancers.

In conclusion, a new approach for RNAi gene silencing using a VEGF siRNA/poly(CBA-DAH-R) polyplex delivery system has been demonstrated. The siRNA/poly(CBA-DAH-R) polyplexes successfully localize siRNA to the cytoplasm due to the reductive degradation of the polymers. In addition to the feature of triggered release, arginine modification of poly(CBA-DAH-R) enhances cellular permeability, leading to effective down regulation of VEGF expression in various human cancer cells. Since the siRNA/poly(CBA-DAH-R) polyplex formulation has low cytotoxicity, high efficiency in target gene silencing, and broad efficacy in various cell types, the siRNA/poly(CBA-DAH-R) polyplex offers a broad range of potential applications for delivering therapeutic siRNAs.

Example 15

Cancer Treatment

In this example, VEGF siRNA (SEQ ID NO:1 and SEQ ID NO:2) is complexed with poly(CBA-DAH-R), and the resulting complex is administered to a patient in need of cancer treatment. The complex circulates systemically in the body of the patient until it contacts and is internalized in a cancer cell. In the reducing environment of the cytoplasm of the cell, the poly(CBA-DAH-R) portion of the complex is degraded, releasing the VEGF siRNA. The VEGF siRNA then silences the expression of the cancer cell's VEGF gene by RNA interference, thus providing a treatment for the patient's cancer.

The invention claimed is:

1. A complex comprising an siRNA bonded to an arginine-grafted bioreducible polymer, wherein the arginine-grafted bioreducible polymer is represented by the formula

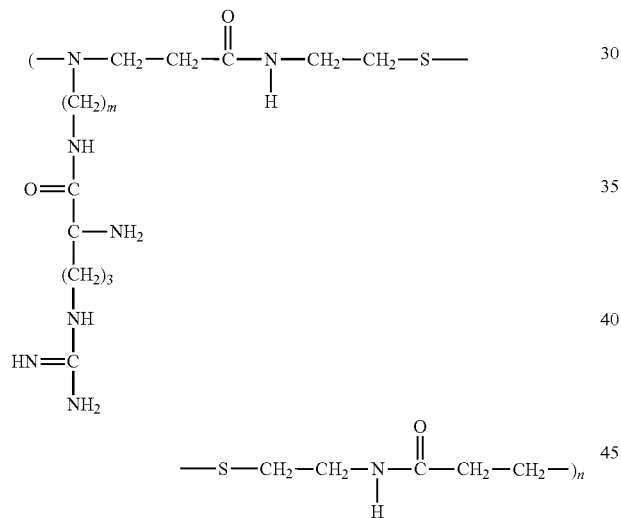

wherein n is about 1 to about 1000 and m is about 1 to about 18.

2. The complex of claim 1 wherein m is 6.

3. The complex of claim 1 wherein m is 4.

4. The complex of claim 1 wherein m is 2.

5. The complex of claim 1 wherein the siRNA is targeted to vascular endothelial growth factor.

6. The complex of claim 5 wherein the siRNA has a nucleotide sequence as in SEQ ID NO:1 or SEQ ID NO:2.

* * * * *

SEQUENCE LISTING

<160> NUMBER OF SEQ ID NOS: 4

<210> SEQ ID NO 1
<211> LENGTH: 21
<212> TYPE: DNA
<213> ORGANISM: Homo sapiens

<400> SEQUENCE: 1
ggaguacccu gaugagauct t                                                 21

<210> SEQ ID NO 2
<211> LENGTH: 21
<212> TYPE: DNA
<213> ORGANISM: Homo sapiens

<400> SEQUENCE: 2

```
gaucucauca ggguacucct t                                              21

<210> SEQ ID NO 3
<211> LENGTH: 21
<212> TYPE: DNA
<213> ORGANISM: Aequorea victoria

<400> SEQUENCE: 3
gcacgacuuc uucaaguccu t                                              21

<210> SEQ ID NO 4
<211> LENGTH: 21
<212> TYPE: DNA
<213> ORGANISM: Aequorea victoria

<400> SEQUENCE: 4
ggacuugaag aagucgugct t                                              21
```